(12) United States Patent
McAuliffe et al.

(10) Patent No.: US 8,282,688 B2
(45) Date of Patent: Oct. 9, 2012

(54) LACCASE MEDIATORS AND METHODS OF USE

(75) Inventors: Joseph C. McAuliffe, Palo Alto, CA (US); Huaming Wang, Fremont, CA (US)

(73) Assignee: Danisco US Inc., Palo Alto, CA (US)

( * ) Notice: Subject to any disclaimer, the term of this patent is extended or adjusted under 35 U.S.C. 154(b) by 197 days.

(21) Appl. No.: 11/954,863

(22) Filed: Dec. 12, 2007

(65) Prior Publication Data

US 2008/0189871 A1    Aug. 14, 2008

Related U.S. Application Data

(60) Provisional application No. 60/875,518, filed on Dec. 18, 2006, provisional application No. 60/875,454, filed on Dec. 18, 2006.

(51) Int. Cl.
*D06L 3/11* (2006.01)
(52) U.S. Cl. ........ 8/107; 8/102; 8/111; 8/115; 8/115.61; 8/181; 8/192
(58) Field of Classification Search .............. 8/111, 102, 8/107, 115, 115.61, 181, 192; 510/303, 305, 510/306, 367, 369, 392
See application file for complete search history.

(56) References Cited

U.S. PATENT DOCUMENTS

| | | | |
|---|---|---|---|
| 5,752,980 A * | 5/1998 | Pedersen et al. ................. 8/111 |
| 5,861,271 A | 1/1999 | Fowler et al. | |
| 5,908,472 A | 6/1999 | Vollmond | |
| 7,105,032 B2 * | 9/2006 | Gross et al. .................... 8/405 |
| 7,135,184 B2 * | 11/2006 | Tsujino et al. ............ 424/195.15 |
| 7,300,472 B2 * | 11/2007 | Gross et al. .................... 8/405 |
| 7,413,877 B2 | 8/2008 | Collier et al. | |
| 7,413,887 B2 | 8/2008 | Dunn-Coleman et al. | |
| 2005/0089980 A1 * | 4/2005 | Kruus et al. ................. 435/189 |

FOREIGN PATENT DOCUMENTS

| | | |
|---|---|---|
| EP | 0 238 023 A2 | 9/1987 |
| EP | 0 504 005 A1 | 9/1992 |
| JP | 02238885 A2 | 9/1990 |
| WO | WO 92/01046 A1 | 1/1992 |
| WO | WO 95/01426 A1 | 1/1995 |
| WO | WO 95/33836 A1 | 12/1995 |
| WO | WO 95/33837 A1 | 12/1995 |
| WO | WO 96/00787 A1 | 1/1996 |
| WO | WO 96/12845 A1 | 5/1996 |
| WO | WO 97/08325 A2 | 3/1997 |
| WO | WO 97/11217 * | 3/1997 |
| WO | WO 97/11217 A1 | 3/1997 |

OTHER PUBLICATIONS

Altschul, S.F. et al. "Basic local alignment search tool." *J. Mol. Biol* 215(3): 403-410, 1990.
Altschul, S.F. et al. "Gapped Blast and PSI—BLAST: a new generation of protein database search programs." *Nucleic Acids Res.* 25: 3389-3402, 1997.
U.S. Appl. No. 60/875,518, filed Dec. 18, 2006, Wang.
U.S. Appl. No. 60/984,430, filed Nov. 1, 2007, Bao et al.
Mander, G.J. et al. "Use of Laccase as a Novel, Versatile Reporter System in Filamentous Fungi." *Appl. Environ. Microbiol.* 72(7): 5020-5026, Jul. 1, 2006.

* cited by examiner

*Primary Examiner* — Lorna M Douyon
*Assistant Examiner* — Amina Khan
(74) *Attorney, Agent, or Firm* — Danisco US Inc.

(57) ABSTRACT

Novel laccase mediators, including carboxyamido and cyano derivatives of 2,6-dimethoxyphenol that exhibit improved hydrolytic stability and good bleaching performance. The novel laccase enzymes may be employed in conjunction with the 2,6-dimethoxyphenol derivatives of this invention to provide an improved method for bleaching denim fabrics.

22 Claims, 7 Drawing Sheets

Figure 2. Bleaching of soluble indigo using a *Thielavia* sp. laccase and a variety of mediators at 50 and 500 uM concentrations.
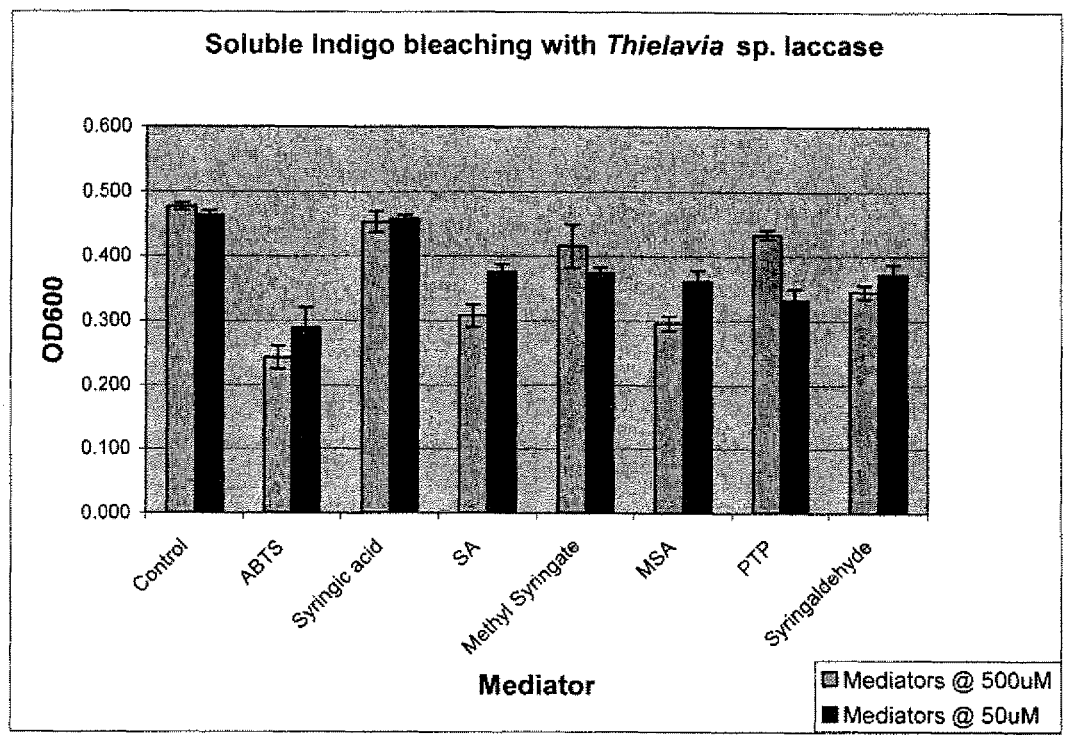

Figure 3. Bleaching of soluble indigo using a *Thielavia*, *Myceliophthora* and *Cerrena* sp. laccase and a variety of mediators at pH 5.
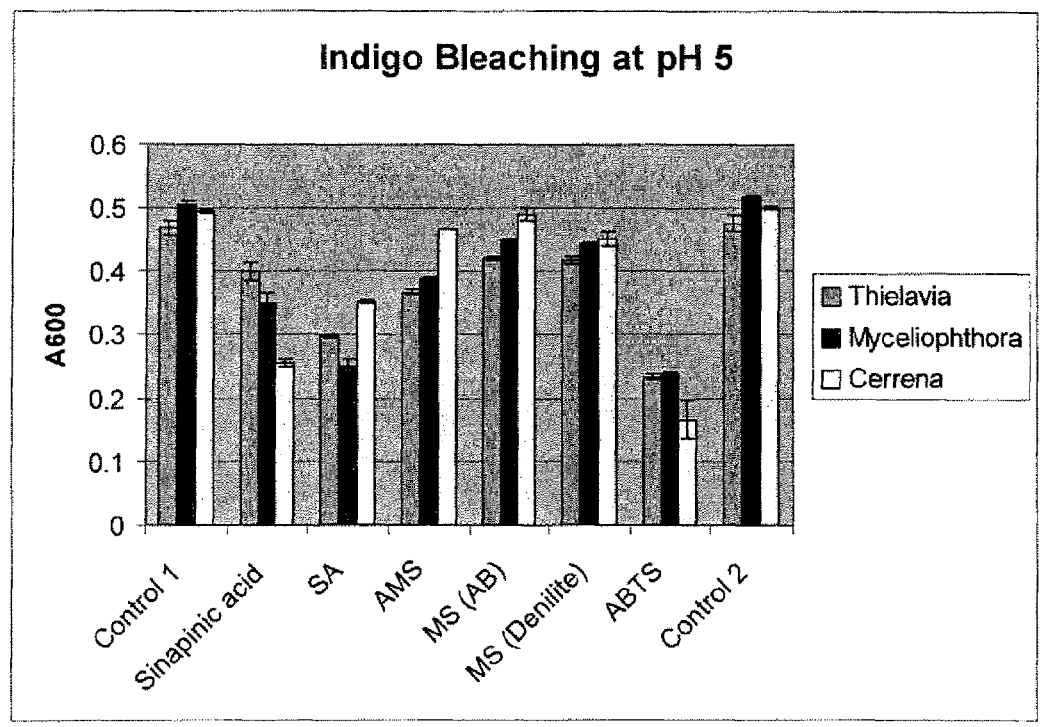

Figure 4. Bleaching of soluble indigo using a *Thielavia*, *Myceliophthora* and *Cerrena* sp. laccase and a variety of mediators at pH 7.
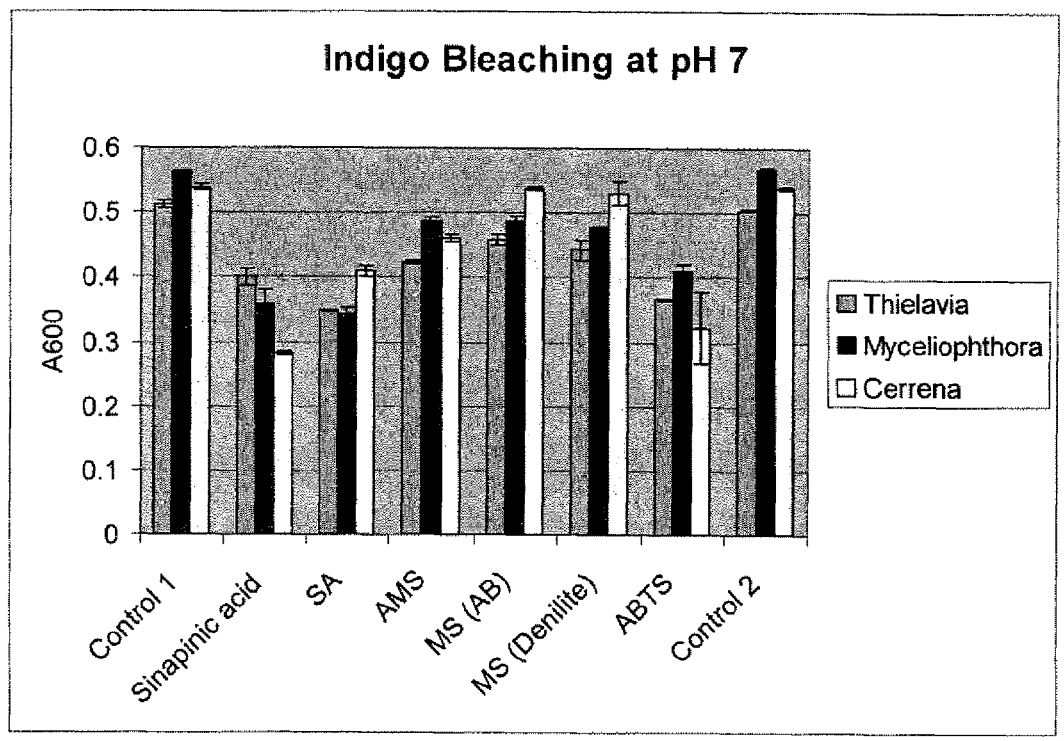

Figure 5. Total color difference (E) of denim swatches (frontside) treated with *C. unicolor* laccase (20 ppm) and 3 mediators at various concentrations.
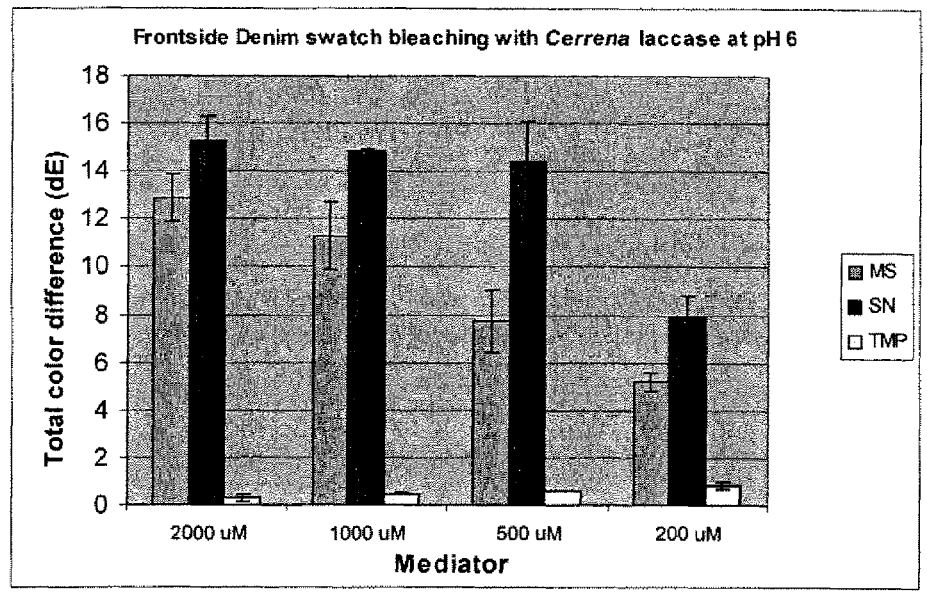
Figure 6. Total color difference (E) of denim swatches (backside) treated with *C. unicolor* laccase (20 ppm) and 3 mediators at various concentrations.
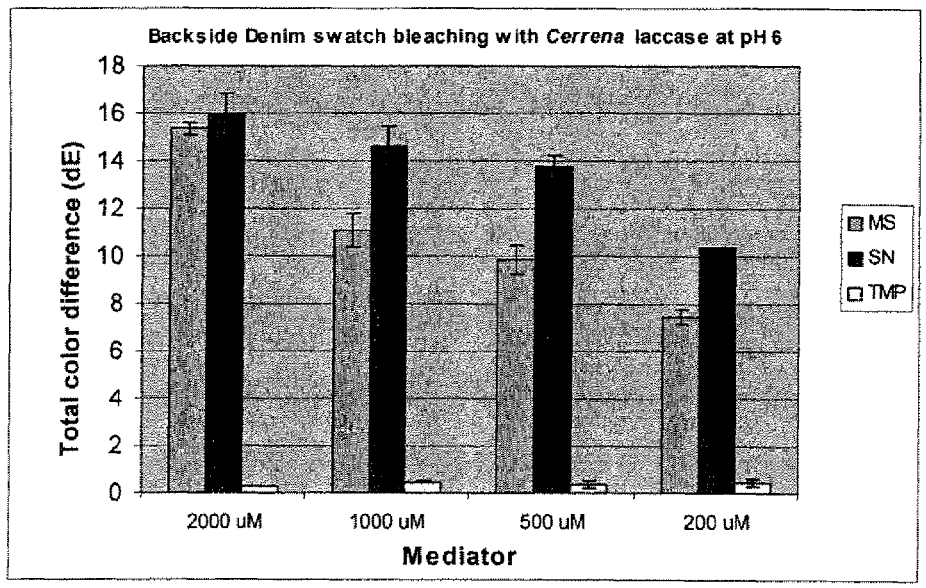

Figure 7. Total color differences for bleached denim disks (frontside) as a function of laccase/mediator combinations using laccase D from *C. unicolor*.
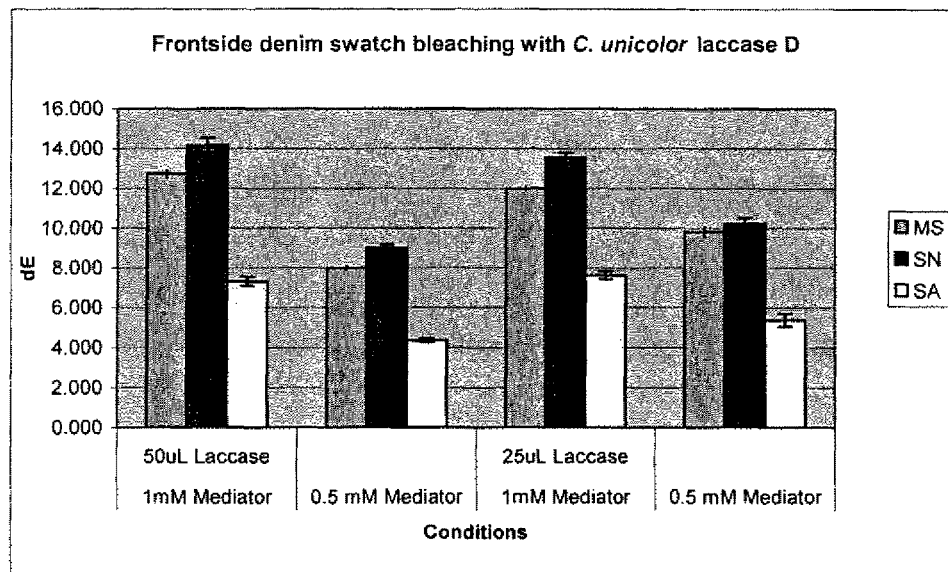
Figure 8. Total color differences for bleached denim disks (backside) as a function of laccase/mediator combinations using laccase D from *C. unicolor*.
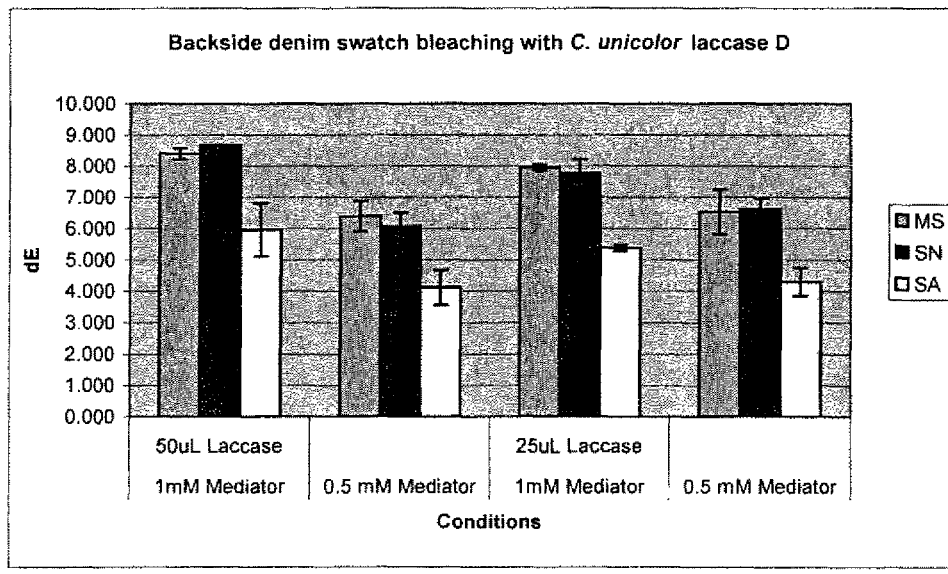

LACCASE MEDIATORS AND METHODS OF USE

CROSS-REFERENCE TO RELATED APPLICATIONS

The present application claims priority to U.S. Provisional Patent Application Ser. No. 60/875,518, entitled "Novel Laccases, Compositions and Methods of Use", filed 18 Dec. 2006 and U.S. Provisional Patent Application Ser. No. 60/875,454, entitled "Laccase Mediators and Methods of Use", filed 18 Dec. 2006.

FIELD OF THE INVENTION

The present invention relates to hydrolytically stable laccase mediators, and to enzymatic methods for bleaching materials.

BACKGROUND OF THE INVENTION

Laccases are copper-containing enzymes that are known to be good oxidizing agents in the presence of oxygen. Laccases are found in microbes, fungi, and higher organisms. Laccase enzymes are used for many applications, including pulp and textiles bleaching, treatment of pulp waste water, de-inking, industrial color removal, bleaching laundry detergents, oral care teeth whiteners, and as catalysts or facilitators for polymerization and oxidation reactions.

Laccases can be utilized for a wide variety of applications in a number of industries, including the detergent industry, the paper and pulp industry, the textile industry and the food industry. In one application, phenol oxidizing enzymes are used as an aid in the removal of stains, such as food stains, from clothes during detergent washing.

Most laccases exhibit pH optima in the acidic pH range while being inactive in neutral or alkaline pHs.

Laccases are known to be produced by a wide variety of fungi, including species of the genii *Aspergillus, Neurospora, Podospora, Botrytis, Pleurotus, Formes, Phlebia, Trametes, Polyporus, Stachybotrys, Rhizoctonia, Bipolaris, Curvularia, Amerosporium*, and *Lentinus*. However, there remains a need for laccases having different performance profiles in various applications.

For many applications, the oxidizing efficiency of a laccase can be improved through the use of a mediator, also known as an enhancing agent. Systems that include a laccase and a mediator are known in the art as laccase-mediator systems (LMS). The same compounds can also be used to activate or initiate the action of laccase.

There are several known mediators for use in a laccase-mediator system. These include HBT (1-hydroxybenzotriazole), ABTS [2,2'-azinobis(3-ethylbenzothiazoline-6-sulfinic acid)], NHA (N-hydroxyacetanilide), NEIAA (N-acetyl-N-phenylhydroxylamine), HBTO (3-hydroxy 1,2,3-benzotriazin-4(3H)-one), and VIO (violuric acid). In addition, there are several compounds containing NH—OH or N—O that have been found to be useful as mediators.

Functional groups and substituents have large effects on mediator efficiency. Even within the same class of compounds, a substituent can change the laccase specificity towards a substrate, thereby increasing or decreasing mediator efficiency greatly. In addition, a mediator may be effective for one particular application but unsuitable for another application. Another drawback for current mediators is their tendency to polymerize during use. Thus, there is a need to discover efficient mediators for specific applications. One such application is the bleaching of textiles, wherein it is also important that the mediators are not unduly expensive or hazardous. Other applications of the laccase-mediator system are given below.

Thus, there is a need to identify additional mediators that activate laccase, and/or enhance the activity of enzymes that exhibit laccase activity.

SUMMARY OF THE INVENTION

Described herein are novel laccase mediators, including 4-carboxamido and 4-cyano derivatives of 2,6-dimethoxyphenol, that exhibit improved stability and good bleaching performance.

In an embodiment the novel laccase enzymes are employed in conjunction with the 4-substituted 2,6-dimethoxyphenol derivatives of this invention to provide an improved method for bleaching denim fabrics.

BRIEF DESCRIPTION OF THE FIGURES

FIG. 2 is a bar graph showing the results of bleaching soluble indigo using a *Thielavia* sp. laccase and a variety of mediators at 50 and 500 uM concentrations.

FIG. 3 is a bar graph showing the results of bleaching soluble indigo using a *Thielavia, Myceliophthora* and *Cerrena* sp. laccase and a variety of mediators at pH 5.

FIG. 4 is a bar graph showing the results of bleaching soluble indigo using a *Thielavia, Myceliophthora* and *Cerrena* sp. laccase and a variety of mediators at pH 7.

FIG. 5 is a bar graph showing the total color difference (E) of denim swatches (front side) treated with *C. unicolor* laccase (20 ppm) and 3 mediators at various concentrations.

FIG. 6 is a bar graph showing the total color difference (E) of denim swatches (backside) treated with *C. unicolor* laccase (20 ppm) and 3 mediators at various concentrations.

FIG. 7 is a bar graph showing the total color differences for bleached denim disks (frontside) as a function of laccase/mediator combinations using laccase D from *C. unicolor*.

FIG. 8 is a bar graph showing the total color differences for bleached denim disks (backside) as a function of laccase/mediator combinations using laccase D from *C. unicolor*.

DETAILED DESCRIPTION OF THE INVENTION

Figure 1:
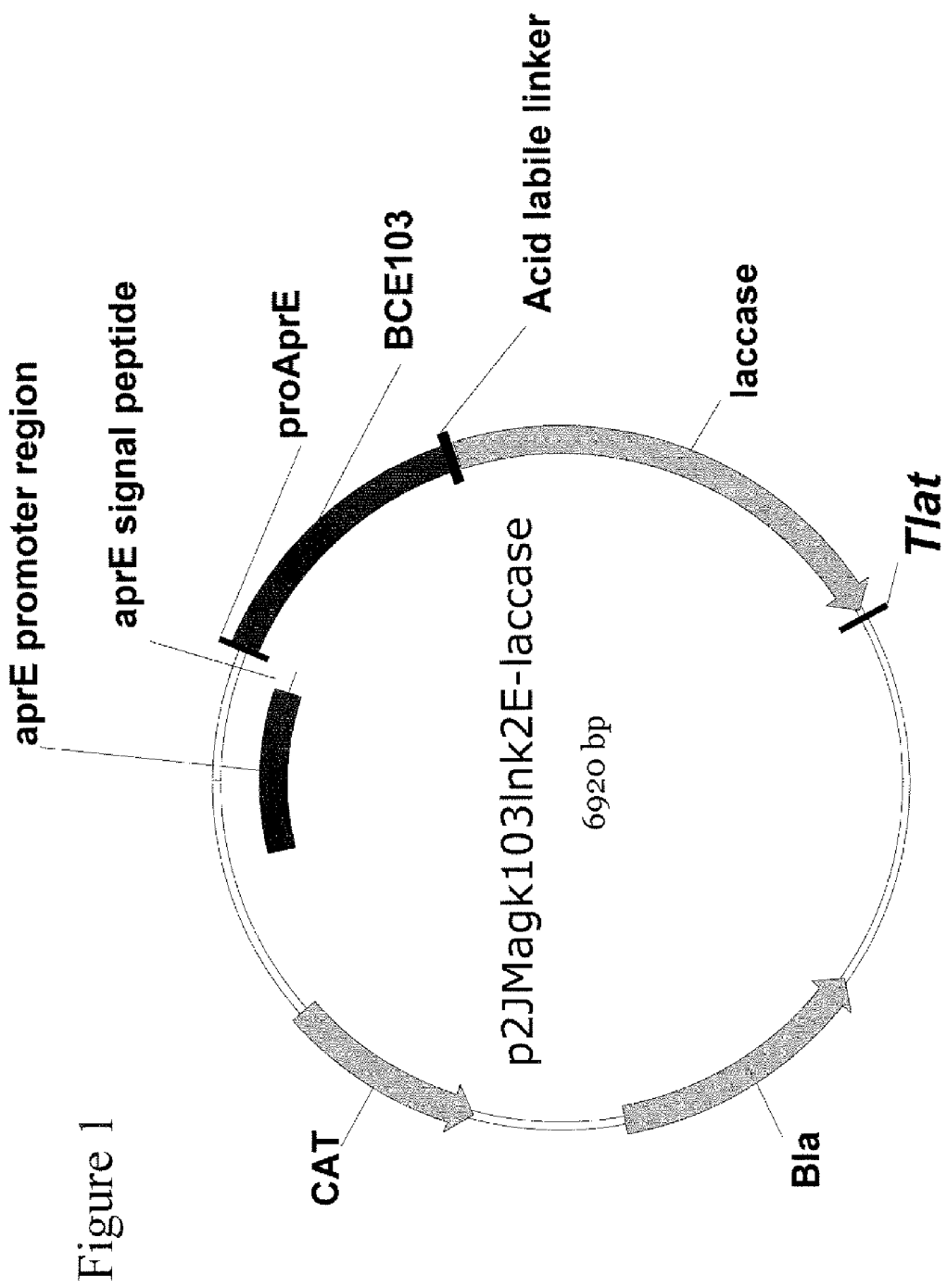
FIG. 1 is a schematic of the *Bacillus* expression plasmid (p2JMagk103Ink2E-laccase) for codon optimized laccase D gene fused to the gene encoding BCE103, used in Example 1.

Unless defined otherwise herein, all technical and scientific terms used herein have the same meaning as commonly understood by one of ordinary skill in the art to which this invention belongs. Singleton, et al., DICTIONARY OF MICROBIOLOGY AND MOLECULAR BIOLOGY, 2D ED., John Wiley and Sons, New York (1994), and Hale & Marham, THE HARPER COLLINS DICTIONARY OF BIOLOGY, Harper Perennial, N.Y. (1991) provide one of skill with a general dictionary of many of the terms used in this invention. Although any methods and materials similar or equivalent to those described herein can be used in the practice or testing of the present invention, the preferred methods and materials are described. Numeric ranges are inclusive of the numbers defining the range. It is to be understood that this invention is not limited to the particular methodology, protocols, and reagents described, as these may vary.

The headings provided herein are not limitations of the various aspects or embodiments of the invention which can be had by reference to the specification as a whole. Accordingly, the terms defined immediately below are more fully defined by reference to the specification as a whole.

All publications cited herein are expressly incorporated herein by reference for the purpose of describing and disclosing compositions and methodologies which might be used in connection with the invention.

I. Laccase and Laccase Related Enzymes

In the context of this invention, laccases and laccase related enzymes contemplate any laccase enzyme comprised by the enzyme classification (EC 1.10.3.2). The laccase enzymes are known from microbial and plant origin. The microbial laccase enzyme may be derived from bacteria or fungi (including filamentous fungi and yeasts) and suitable examples include a laccase derivable from a strain of *Aspergillus, Neurospora*, e.g. *N. crassa, Podospora, Botrytis, Collybia, Cerrena, Stachybotrys, Panus*, e.g., *Panus rudis, Theilava, Fomes, Lentinus, Pleurotus, Trametes*, e.g. *T. villosa* and *T. versicolor, Rhizoctonia*, e.g. *R. solani, Coprinus*, e.g. *C. plicatilis* and *C. cinereus, Psatyrella, Myceliophthora*, e.g. *M. thermonhila, Schytalidium, Phlebia*, e.g., *P. radita* (WO 92/01046), or *Coriolus*, e.g. *C. hirsutus* (JP 2-238885), *Spongipellis* sp., *Polyporus, Ceriporiopsis subvermispora, Ganoderma tsunodae* and *Trichoderma*.

The laccase or the laccase related enzyme may furthermore be produced by a method comprising cultivating a host cell transformed with a recombinant DNA vector which carries a DNA sequence encoding said laccase as well as DNA sequences permitting the expression of the DNA sequence encoding the laccase, in a culture medium under conditions permitting the expression of the laccase enzyme, and recovering the laccase from the culture.

The expression vector may be transformed into a suitable host cell, such as a fungal cell, preferred examples of which are species of *Aspergillus*, most preferably *Aspergillus oryzae* and *Aspergillus niger*, and species of *Fusarium*, most preferably *Fusarium venenatum*. Fungal cells may be transformed by a process involving protoplast formation and transformation of the protoplasts followed by regeneration of the cell wall in a manner known per se. The use of *Aspergillus* as a host microorganism is described in EP 238,023. The use of *Fusarium* as a host microorganism is described in WO 96/00787 and WO 97/08325.

Alternatively, the host organism may be a bacterium, in particular strains of *Bacillus, Pseudomonas, Streptomyces*, or *E. coli*. The transformation of bacterial cells may be performed according to conventional methods, e.g., as described in T. Maniatis et al., Molecular Cloning: A Laboratory Manual, Cold Spring Harbor, 1982. The screening of appropriate DNA sequences and construction of vectors may also be carried out by standard procedures, cf. T. Maniatis et al., op. cit.

The medium used to cultivate the transformed host cells may be any conventional medium suitable for growing the host cells in question. The expressed enzyme may conveniently be secreted into the culture medium and may be recovered therefrom by well-known procedures including separating the cells from the medium by centrifugation or filtration, precipitating proteinaceous components of the medium by means of a salt such as ammonium sulphate, followed by chromatographic procedures such as ion exchange chromatography, affinity chromatography, or the like.

In an embodiment, the expression host may be a *Trichoderma reesei* with the laccase coding region under the control of a CBH1 promoter and terminator. (See, e.g., U.S. Pat. No. 5,861,271). The expression vector may be pTrex3g, as disclosed in U.S. patent application Ser. No. 11/245,628 filed 7 Oct. 2005.

In this manner the following novel genes and laccases were prepared:

```
A. Cellena laccase D1 gene from CBS154.29 strain
(SEQ ID No. 1)
GATTCTAATA GACCAGGCAT ACCAAGAGAT CTACAGGTTG ACAGACCATT    50

CTTCTAGGCG GCATTTATGC TGTAGCGTCA GAAATTATCT CTCCATTTGT   100

ATCCCACAGG TCCTGTAATA ACACGGAGAC AGTCCAAACT GGGATGCCTT   150

TTTTCTCAAC TATGGGCGCA CATAGTCTGG ACGATGGTAT ATAAGACGAT   200

GGTATGAGAC CCATGAAGTC AGAACACTTT TGCTCTCTGA CATTTCATGG   250

TTCACACTCT CGAGATGGGA TTGAACTCGG CTATTACATC GCTTGCTATC   300

TTAGCTCTGT CAGTCGGAAG CTATGCTGCA ATTGGGCCCG TGGCCGACAT   350

ACACATTGTC AACAAAGACC TTGCTCCAGA TGGCGTACAA CGTCCAACCG   400

TGCTTGCCGG AGGCACTTTT CCTGGGACGT TGATCACCGG TCAGAAAGTA   450

AGGGATATTA GTTTGCGTCA AAGAGCCAAC CAAAACTAAC CGTCCCGTAC   500

TATAGGGTGA CAACTTCCAG CTCAATGTCA TCGATGATCT TACCGACGAT   550

CGGATGTTGA CGCCAACTTC CATTGTGAGC CTATTATTGT ATGATTTATC   600

CGAATAGTTT CGCAGTCTGA TCATTGGATC TCTATCGCTA GCATTGGCAC   650

GGTTTCTTCC AGAAGGGAAC CGCTTGGGCC GACGGTCCCG CCTTCGTAAC   700

TCAGTGCCCT ATAATAGCAG ATAACTCTTT TCTGTATGAC TTCGACGTCC   750

CAGACCAAGC TGGTACTTTC TGGTATCATA GTCATCTATC CACTCAGTAC   800
```

-continued

```
TGTGACGGTT TACGTGGTGC CTTCGTTGTG TACGATCCTA ACGATCCTCA  850
CAAAGACCTA TACGATGTTG ATGACGGTGG GTTCCAAATA TTTGTTCTGC  900
AGACATTGTA TTGACGGTGT TCATTATAAT TTCAGAGAGC ACCGTGATTA  950
CCCTTGCGGA TTGGTACCAT GTTCTCGCCC AGACCGTTGT CGGCGCTGCG 1000
TGAGTAACAC ATACACGCGC TCCGGCACAC TGATACTAAT TTTTTTTTAT 1050
TGTAGCACTC CTGATTCTAC CTTGATCAAC GGGTTAGGCC GTTCACAGAC 1100
CGGACCCGCT GATGCTGAGC TGGCTGTTAT CAGCGTTGAA CATAACAAAC 1150
GGTATGTCAT CTCTACCCAG TATCTTCTCT CCTGCTCTAA TTCGCTGTTT 1200
CACCATAGAT ACCGTTTCCG TTTGGTTTCG ATTTCGTGCG ACCCCAACTT 1250
TACCTTCTCC GTTGATGGTC ATAATATGAC TGTCATCGAA GTCGATGGTG 1300
TCAACACACG ACCCCTGACC GTTGACTCTA TTCAAATCTT CGCCGGACAG 1350
AGGTATTCCT TTGTCGTAAG TTAATCGATA TATTCTCCTT ATTACCCCTG 1400
TGTAATTGAT GTCAATAGCT CAATGCTAAC CAACCCGAAG ACAATTACTG 1450
GATCCGTGCT ATGCCAAACA TCGGTAGAAA TACAACAACA CTGGACGGAA 1500
AGAATGCCGC TATCCTTCGA TACAAGAATG CTTCTGTAGA AGAGCCCAAG 1550
ACCGTTGGGG GCCCCGCTCA ATCCCCGTTG AATGAAGCGG ACCTGCGTCC 1600
ACTCGTACCT GCTCCTGTGG TATGTCTTGT CGCGCTGTTC CATCGCTATT 1650
TCATATTAAC GTTTTGTTTT TGTCAAGCCT GGAAACGCTG TTCCAGGTGG 1700
CGCAGACATC AATCACAGGC TTAACTTAAC TTTCGTACGT ACACCTGGTT 1750
GAAACATTAT ATTTCCAGTC TAACCTCTCT TGTAGAGTAA CGGCCTCTTC 1800
AGCATCAACA ACGCCTCCTT CACTaATCCT TCGGTCCCCG CCTTATTACA 1850
AATTCTGAGC GGTGCTCAGA ACGCTCAAGA TTTACTTCCA ACGGGTAGTT 1900
ACATTGGCCT TGAACTAGGC AAGGTTGTGG AGCTCGTTAT ACCTCCTCTG 1950
GCAGTTGGAG GACCGCACCC TTTCCATCTT CATGGCGTAA GCATACCACA 2000
CTCCCGCAGC CAGAATGACG CAAACTAATC ATGATATGCA GCACAATTTC 2050
TGGGTCGTCC GTAGTGCAGG TAGCGATGAG TATAACTTTG ACGATGCTAT 2100
CCTCAGGGAC GTCGTRAGCA TTGGAGCGGG GACTGATGAA GTCACAATCC 2150
GTTTCGTGGT ATGTCTCACC CCTCGCATTT TGAGACGCAA GAGCTGATAT 2200
ATTTTAACAT AGACCGACAA TCCGGGCCCG TGGTTCCTCC ATTGCCATAT 2250
TGATTGGCAT TTGGAGGCAG GCCTTGCCAT CGTCTTCGCT GAGGGCATCA 2300
ATCAGACCGC TGCAGCCAAC CCAACACCCC GTACGTGACA CTGAGGGTTT 2350
CTTTATAGTG CTGGATTACT GAATCGAGAT TTCTCCACAG AAGCATGGGA 2400
TGAGCTTTGC CCCAAATATA ACGGGTTGAG TGCGAGCCAG AAGGTCAAGC 2450
CTAAGAAAGG AACTGCTATT TAAACGTGGT CCTAGACTAC GGGCATATAA 2500
GTATTCGGGT AGCGCGTGTG AGCAATGTTC CGATACACGT AGATTCATCA 2550
CCGGACACGC TGGGACAATT TGTGTATAAT GGCTAGTAAC GTATCTGAGT 2600
TCTGGTGTGT AGTTCAAAGA GACAGCCCTT CCTGAGACAG CCCTTCCTGA 2650
GACAGCCCTT CCTGAGACGT GACCTCCGTA GTCTGCACAC GATACTYCTA 2700
AATACGTATG GCAAGATGAC AAAGAGGAGG ATGTGAGTTA CTACGAACAG 2750
```

-continued

```
AAATAGTGCC CGGCCTCGGA GAGATGTTCT TGAATATGGG ACTGGGACCA 2800

ACATCCGGA                                              2809
``` encoding the enzyme laccase D1, having the translated
protein sequence (SEQ ID No. 2)

```
MGLNSAITSL AILALSVGSY AAIGPVADIH IVNKDLAPDG VQRPTVLAGG   50
TFPGTLITGQ KGDNFQLNVI DDLTDDRMLT PTSIHWHGFF QKGTAWADGP  100
AFVTQCPIIA DNSFLYDFDV PDQAGTFWYH SHLSTQYCDG LRGAFVVYDP  150
NDPHKDLYDV DDGGTVITLA DWYHVLAQTV VGAATPDSTL INGLGRSQTG  200
PADAELAVIS VEHNKRYRFR LVSISCDPNF TFSVDGHNMT VIEVDGVNTR  250
PLTVDSIQIF AGQRYSFVLN ANQPEDNYWI RAMPNIGRNT TTLDGKNAAI  300
LRYKNASVEE PKTVGGPAQS PLNEADLRPL VPAPVPGNAV PGGADINHRL  350
NLTFSNGLFS INNASFTNPS VPALLQILSG AQNAQDLLPT GSYIGLELGK  400
VVELVIPPLA VGGPHPFHLH GHNFWVVRSA GSDEYNFDDA ILRDVVSIGA  450
GTDEVTTRFV TDNPGPWFLH CHIDWHLEAG LAIVFAEGIN QTAAANPTPQ  500
AWDELCPKYN GLSASQKVKP KKGTAI                           526
```

B. *Cerrena laccase* D2 gene from CBS115.075 strain
(SEQ ID No. 3)

```
GATCTGGACG ATGGTATATA AGACGATGGT ATGAGACCCA TGAAGTCTGA   50
ACACTTTTGC TCTCTGACAT TTCATGGTTC ATACTCTCGA GATGGGATTG  100
AACTCGGCTA TTACATCGCT TGCTATCTTA GCTCTGTCAG TCGGAAGCTA  150
TGCTGCAATT GGGCCCGTGG CCGACATACA CATTGTCAAC AAAGACCTTG  200
CTCCAGATGG TGTACAACGT CCAACCGTGC TCGCCGGAGG CACTTTTCCT  250
GGGACGTTGA TCACCGGTCA GAAAGTAAGG AATATTAGTT TGCGTCAAAG  300
AGCCAACCAA AATTAACCGT CCCGTCCCAT AGGGTGACAA CTTCCAGCTC  350
AATGTCATTG ATGATCTTAC CGACGATCGG ATGTTGACAC CAACTTCCAT  400
TGTGAGCCTA TTATTGTATG ATTTATCCGT ATAGTTTCTC AGTCTGATCA  450
TTGGCTCTCT ATCGCTAGCA TTGGCACGGT TTCTTCCAGA AGGGAACCGC  500
TTGGGCCGAC GGTCCCGCCT TCGTAACTCA GTGCCCTATA ATAGCAGATA  550
ACTCTTTTCT GTATGACTTC GACGTCCCCG ACCAAGCTGG TACTTTCTGG  600
TATCATAGTC ATCTATCCAC TCAGTACTGT GACGGTTTAC GTGGTGCCTT  650
CGTTGTGTAC GATCCTAACG ATCCTCACAA AGACCTATAC GATGTTGATG  700
ACGGTGGGTT CCAAATACTT GACCAAGAAA CATTATATTG ATAGTATCCA  750
CTCTGATTTT CAGAGAGCAC CGTGATTACC CTTGCGGATT GGTACCATGT  800
TCTCGCCCAG ACCGTTGTCG GCGCTGCGTG AGTAACACAT ACACGCGCTC  850
CGGCACACTG ATACTAATTT TTTATTGTAG CACTCCTGAT TCTACCTTGA  900
TCAACGGGTT AGGCCGTTCA CAGACCGGAC CCGCTGATGC TGAGCTGGCT  950
GTTATCAGCG TTGAACATAA CAAACGGTAT GTCATCTCTA CCCATTATCT 1000
TCTCTCCTGC TTTAATTCGC TGTTTCACCA TAGATACCGA TTCCGTTTGG 1050
TTTCGATTTC GTGCGACCCC AACTTTACCT TCTCCGTTGA TGGTCATAAT 1100
ATGACTGTCA TCGAAGTCGA CGGTGTCAAC ACACGACCCC TGACCGTTGA 1150
CTCTATTCAA ATCTTCGCCG GACAGAGGTA TTCCTTTGTC GTAAGTTAAT 1200
CGATATATTC TCCCTATTAC CCCTGTGTAA TTGATGTCAA CAGCTCAATG 1250
```

```
CTAACCAACC CGACGACAAT TACTGGATCC GTGCTATGCC AAACATCGGT  1300

AGAAATACAA CAACACTGGA CGGAAAGAAT GCCGCTATCC TTCGATACAA  1350

GAATGCTTCT GTAGAAGAGC CCAAGACCGT TGGGGGCCCC GCTCAATCCC  1400

CGTTGAATGA AGCGGACCTG CGTCCACTCG TACCTGCTCC IGTGGTATGT  1450

CTTGTCGTGC TGTTCCATCG CTATTTCATA TTAACGTTTT GTTTTTGTCA  1500

AGCCTGGAAA CGCTGTTCCA GGTGGCGCAG ACATCAATCA CAGGCTTAAC  1550

TTAACTTTCG TACGTACACC TGGTTGAAAC ATTATATTTC CAGTCTAACC  1600

TCTTGTAGAG TAACGGCCTT TTCAGCATCA ACAACGCCTC CTTCACTAAT  1650

CCTTCGGTCC CCGCCTTATT ACAAATTCTG AGCGGTGCTC AGAACGCTCA  1700

AGATTTACTT CCAACGGGTA GTTACATTGG CCTTGAACTA GGCAAGGTTG  1750

TGGAGCTCGT TATACCTCCT CTGGCAGTTG GAGGACCGCA CCCTTTCCAT  1800

CTTCATGGCG TAAGCATACC ACACTCCCGC AGCCAGAATG ACGCAAACTA  1850

ATCATGATAT GCAGCACAAT TTCTGGGTCG TCCGTAGTGC AGGTAGCGAT  1900

GAGTATAACT TTGACGATGC TATCCTCAGG GACGTCGTGA GCATTGGAGC  1950

GGGGACTGAT GAAGTCACAA TCCGTTTCGT GGTATGTCTC ACCCCTCGCA  2000

TTTTGAGACG CAAGAGCTGA TATATTTTAA CATAGACCGA CAATCCGGGC  2050

CCGTGGTTCC TCCATTGCCA TATTGATTGG CATTTGGAGG CAGGCCTTGC  2100

CATCGTCTTC GCTGAGGGCA TCAATCAGAC CGCTGCAGCC AACCCAACAC  2150

CCCGTACGTG ACACTGAGGG TTTCTTTATA GTGCTGGATT ACTGAATCGA  2200

GATTTCTCCA CAGAAGCATG GGATGAGCTT TGCCCCAAAT ATAACGGGTT  2250

GAGTGCGAGC CAGAAGGTCA AGCCTAAGAA AGGAACTGCT ATTTAAACG   2299 encoding the enzyme laccase D2, having the translated
protein sequence (SEQ ID No. 4)
MGLNSAITSL AILALSVGSY AAIGPVADIH IVNKDLAPDG VQRPTVLAGG    50

TFPGTLITGQ KGDNFQLNVI DDLTDDRMLT PTSIHWHGFF QKGTAWADGP   100

AFVTQCPIIA DNSFLYDFDV PDQAGTFWYH SHLSTQYCDG LRGAFVVYDP   150

NDPHKDLYDV DDGGTVITLA DWYHVLAQTV VGAATPDSTL INGLGRSQTG   200

PADAELAVIS VEHNKRYRFR LVSISCDPNF TFSVDGHNMT VIEVDGVNTR   250

PLTVDSIQIF AGQRYSFVLN ANQPDDNYWI RAMPNIGRNT TTLDGKNAAI   300

LRYKNASVEE PKTVGGPAQS PLNEADLRPL VPAPVPGNAV PGGADINHRL   350

NLTFSNGLFS INNASFTNPS VPALLQILSG AQNAQDLLPT GSYIGLELGK   400

VVELVIPPLA VGGPHPFHLH GHNFWVVRSA GSDEYNFDDA ILRDVVSIGA   450

GTDEVTTRFV TDNPGPWFLH CHIDWHLEAG LAIVFAEGIN QTAWDELCPK   500

AWDELCPKYN GLSASQKVKP KKGTAI                            526
```

The term "% identity" herein and refers to the level of nucleic acid or amino acid sequence identity between the nucleic acid sequence that encodes a laccase described herein or the laccase amino acid sequence, when aligned using a sequence alignment program.

For example, as used herein, 80% sequence identity is determined by an algorithm, and accordingly a homologue of a given sequence has greater than 80% sequence identity over a length of the given sequence. Exemplary levels of sequence identity include, but are not limited to, 80, 85, 90, 95, 98% or more sequence identity to a given sequence, e.g., the coding sequence for a laccase, as described herein.

Exemplary computer programs which can be used to determine identity between two sequences include, but are not limited to, the suite of BLAST programs, e.g., BLASTN, BLASTX, and TBLASTX, BLASTP and TBLASTN, publicly available on the Internet at www.ncbi.nlm.nih.gov/BLAST. See also, Altschul, et al., 1990 and Altschul, et al., 1997.

Sequence searches are typically carried out using the BLASTN program when evaluating a given nucleic acid sequence relative to nucleic acid sequences in the GenBank DNA Sequences and other public databases. The BLASTX program is preferred for searching nucleic acid sequences that have been translated in all reading frames against amino acid sequences in the GenBank Protein Sequences and other public databases. Both BLASTN and BLASTX are run using default parameters of an open gap penalty of 11.0, and an extended gap penalty of 1.0, and utilize the BLOSUM-62 matrix. (See, e.g., Altschul, et al., 1997.)

An alignment of selected sequences in order to determine "% identity" between two or more sequences, may be performed using, for example, the CLUSTAL-W program in MacVector version 6.5, operated with default parameters, including an open gap penalty of 10.0, an extended gap penalty of 0.1, and a BLOSUM 30 similarity matrix.

II. Mediators

In an embodiment, the enzymatic oxidation system further comprises one or more chemical mediator agents which enhance the activity of the laccase enzyme. The term "chemical mediator" (or "mediator" may be used interchangeably herein) is defined herein as a chemical compound which acts as a redox mediator to effectively shuttle electrons between the enzyme exhibiting oxidase activity and the dye. Chemical mediators are also known as enhancers and accelerators in the art.

The chemical mediator may be a phenolic compound, for example, methyl syringate, and related compounds, as described in WO 95/01426 and 96/12845. The chemical mediator may also be an N-hydroxy compound, an N-oxime compound, or an N-oxide compound, for example, N-hydroxybenzotriazole, violuric acid, or N-hydroxyacetanilide. The chemical mediator may also be a phenoxazine/phenothiazine compound, for example, phenothiazine-10-propionate. The chemical mediator may further be 2,2'-azinobis-(3-ethylbenzothiazoline-6-sulfonic acid) (ABTS). Other chemical mediators are well known in the art. For example, the compounds disclosed in WO 95/01426 are known to enhance the activity of a laccase. In particular embodiments, the mediator may be acetosyringone, methyl syringate, ethyl syringate, propyl syringate, butyl syringate, hexyl syringate, or octyl syringate.

Preferably, the mediator is 4-cyano-2,6-dimethoxyphenol, 4-carboxamido-2,6-dimethoxyphenol or an N-substituted derivative thereof such as, for example, 4-(N-methyl carboxamido)-2,6-dimethoxyphenol, 4-[N-(2-hydroxyethyl) carboxamido]-2,6-dimethoxyphenol, or 4-(N,N-dimethyl carboxamido)-2,6-dimethoxyphenol.

The mediator used in the present invention may be described by the following formula:

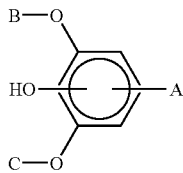

in which formula A is a group such as —R, -D, —CH═CH-D, —CH═CH—CH═CH-D, —CH═N-D, —N═N-D, or —N═CH-D, in which D is selected from the group consisting of —CO-E, —SO$_2$-E, —CN, —NXY, and —N$^+$XYZ, in which E may be —H, —OH, —R, —OR, or —NXY, and X and Y and Z may be identical or different and selected from —H, —OH, —OR and —R; R being a $C_1$-$C_{16}$ alkyl, preferably a $C_1$-$C_8$ alkyl, which alkyl may be saturated or unsaturated, branched or unbranched and optionally substituted with a carboxy, sulfo or amino group; and B and C may be the same or different and selected from $C_mH_{2m+1}$; $1 \leq m \leq 5$.

In an embodiment A in the above mentioned formula is —CN or —CO-E, in which E may be —H, —OH, —R, —OR, or —NXY, where X and Y may be identical or different and selected from —H, —OH, —OR and —R, R being a $C_1$-$C_{16}$ alkyl, preferably a $C_1$-$C_8$ alkyl, which alkyl may be saturated or unsaturated, branched or unbranched and optionally substituted with a carboxy, sulfo or amino group; and B and C may be the same or different and selected from $C_mH_{2m+1}$; $1 \leq m \leq 5$.

In the above mentioned formula A may be placed meta to the hydroxy group d of being placed in the para-position as shown.

In one embodiment the mediator is

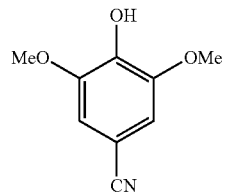

4-Cyano-2,6-dimethoxyphenol

In one embodiment the mediator is

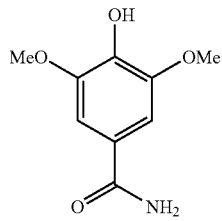

4-Carboxamido-2,6-dimethoxyphenol

In one embodiment the mediator is

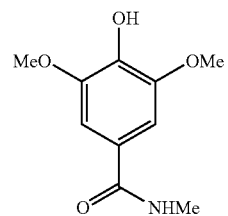

4-(N-Methyl carboxamido)-
2,6-dimethoxyphenol

In one embodiment the mediator is

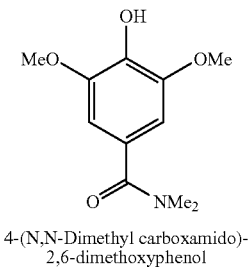

4-(N,N-Dimethyl carboxamido)-
2,6-dimethoxyphenol

In particular embodiments, the mediator may be acetosyringone, methylsyringate, ethylsyringate, propylsyringate, butylsyringate, hexylsyringate, or octylsyringate. Preferably, the mediator is 4-cyano-2,6-dimethoxyphenol, 4-carboxamido-2,6-dimethoxyphenol or a N-substituted derivative thereof such as 4-(N-methyl carboxamido)-2,6-dimethoxyphenol, 4-[N-(2-hydroxyethyl) carboxamido]-2,6-dimethoxyphenol, or 4-(N,N-dimethyl carboxamido)-2,6-dimethoxyphenol or combinations thereof.

The mediator of the invention may be present in concentrations of from 0.005-1000 µmole per g denim, preferably 0.05-500 µmole per g denim, more preferably 0.5-100 µmole per g denim.

The mediators may be prepared by methods known to the skilled artisan, such as those disclosed in WO 97/11217, WO 96/12845 and U.S. Pat. No. 5,752,980.

III. Utility

Industrial applications of laccases include bleaching of pulp and paper and textile bleaching, for example, of indigo-dyed denim fabrics. Laccases have also been found to be useful for hair dyeing (see, e.g., WO 95/33836 and WO 95/33837). European Patent No. 0504005 discloses that laccases can be used for dyeing wool.

The laccases described herein find use in the dyeing and bleaching of textiles, fibers, yarns and the like. The laccases also find use in the treatment of waste water, the delignification of pulp, the depolymerization of high molecular weight aggregates, deinking waste paper, the polymerization of aromatic compounds, radical mediated polymerization and cross-linking reactions (e.g., paints, coatings, biomaterials), and the activation of dyes and to couple organic compounds. The laccases may be used in a cleaning composition or component thereof, or in a detergent.

As described herein, the laccases are capable of oxidizing a wide variety of colored compounds having different chemical structures, using oxygen as the electron acceptor. Accordingly, the laccases presented herein can be used in applications where it is desirable to modify the color associated with colored compounds, such as in cleaning, e.g., for removing the food stains on fabric. In certain situations, a mediator or enhancer can be used to obtain desirable effects.

The laccases presented herein can be used in the field of textiles. For example, the laccases described herein can be used in the treatment, processing, finishing, polishing, or production of fibers, or other fabrics or articles of manufacture. The enzymes herein can be useful, for example, in denim treatment (bleaching work-up processes); in de-coloring indigo waste; in fabric dyeing; in textile bleaching processes; in fiber modification; in achieving enhanced fiber or fabric properties; etc.

The laccases described herein can be used in the leather industry. For example, the laccases can be used in the processing of animal hides including but not limited to de-hairing, liming, bating and/or tanning of hides.

Also disclosed herein is a process for the removal of lignin from lignocellulose-containing material, the bleaching of lignocellulose-containing material (i.e. the enzymatic de-inking of recycled paper) and/or the treatment of waste water arising from the manufacture of paper or cellulose. The process uses laccase enzymes obtained from Cerrena sp., at the same time adding or metering in non-aromatic redox agents plus phenolic and/or non-phenolic aromatic redox compounds, the phenolic and non-phenolic units of the lignin either being oxidized directly by the action of these phenolic and/or non-phenolic aromatic compounds, or the lignin being oxidized by other phenolic and/or non-phenolic compounds produced by the oxidizing action of these compounds.

The laccases described herein can be used in the field of pulp and paper. For example, the laccases can be used in the manufacture of paper pulps and fluff pulps from raw materials such as wood, bamboo, and cereal rice straw; the manufacture of paper and boards for printing and writing, packaging, sanitary and other technical uses; recycling of cellulose fiber for the purpose of making paper and boards; and the treatment of waste products generated by and treated at pulp or paper mills and other facilities specifically dedicated to the manufacture of paper, pulp, or fluff. The enzymes presented herein can be useful, for example, in wood processing; in pulp bleaching; in wood fiber modification; in bio-glue (lignin activation) for MDF manufacturing; for enhanced paper properties; in ink removal; in paper dyeing; in adhesives (e.g. lignin based glue for particle- or fiber boards); etc.

The laccases described herein can be used in the field of feed. For example, the laccases presented herein can be used as a feed additive alone or as part of a feed additive with the aim to increase the nutritional value of feed for any kind of animals such as chicken, cows, pigs, fish and pets; and/or as a processing aid to process plant materials and food industry by products with the aim to produce materials/products suitable as feed raw materials.

The laccases described herein can be used in the field of contact lens cleaning. For example, the laccases can be used in the cleaning, storage, disinfecting, and/or preservation of contact lens.

The laccases described herein can be used in the field of starch. For example, the laccases can be used in the processing of a substrate including starch and/or grain to glucose (dextrose) syrup, fructose syrup or any other syrup, alcohol (potable or fuel) or sugar. Such starch processing may include processing steps such as liquefaction, saccharification, isomerization, and de-branching of a substrate.

The laccases described herein can be used in the field of food. For example, the laccases can be used in the preparation, processing, or as an active ingredient in foods such as yellow fat, tea based beverages, culinary products, bakery, and frozen foods for human consumption. The laccases can be used, for example, as a bread improver, in food preservation, as an oxygen scavenger, etc.

The laccases described herein can be used in the field of personal care. For example, the laccases can be used in the preparation of personal products for humans such as fragrances, and products for skin care, hair care, oral hygiene, personal washing and deodorant and/or antiperspirants, for humans. The enzymes presented herein can be useful, for example, in hair dyeing and/or bleaching, nails dyeing and/or bleaching; skin dyeing and/or bleaching; surface modification (e.g., as coupling reagent); as an anti-microbial agent; in odor removal; teeth whitening; etc.

The laccases described herein can be used in the field of cleaning. For example, the laccases can be used in the cleaning, treatment or care of laundry items such as clothing or fabric; in the cleaning of household hard surfaces; in dishcare, including machine dishwashing applications; and in soap bars and liquids and/or synthetic surfactant bars and liquids. The enzymes presented herein can be useful, for example, in stain removal/de-colorization, and/or in the removal of odors, and/or in sanitization, etc.

The laccases described herein can be used in the field of waste-water treatment. For example, the laccases can be used in decolorization of colored compounds; in detoxification of phenolic components; for anti-microbial activity (e.g., in water recycling); in bio-remediation; etc.

The laccases described herein can be used in the field of bio-materials. For example, the laccases can be used as bio-catalysts for various organic reactions; and/or in connection with biopolymers; in connection with packaging; in connection with adhesives; in surface modification (activation and coupling agent); in production of primary alcohols; in connection with biosensors and/or organic syntheses; etc.

The laccases described herein can be used in the field of anti-microbials. For example, the laccases can be used as an anti-microbial agent in cleaning compositions, or for reducing or eliminating the microbial load of various foods (e.g., meats) or feed.

The laccase mediators can be used as sanitization and antimicrobial agents (e.g., wood protection, detergents). The mediators may be used independently of the enzymes or in conjunction with the enzymes.

As used herein, "cleaning compositions" and "cleaning formulations" refer to compositions that find use in the removal of undesired compounds from items to be cleaned, such as fabric, etc. The term encompasses any materials/compounds selected for the particular type of cleaning composition desired and the form of the product (e.g., liquid, gel, granule, or spray composition), as long as the composition is compatible with the laccase and other enzyme(s) used in the composition. The specific selection of cleaning composition materials are readily made by considering the surface, item or fabric to be cleaned, and the desired form of the composition for the cleaning conditions during use.

The terms further refer to any composition that is suited for cleaning and/or bleaching any object and/or surface. It is intended that the terms include, but are not limited to detergent compositions (e.g., liquid and/or solid laundry detergents and fine fabric detergents; hard surface cleaning formulations, such as for glass, wood, ceramic and metal counter tops and windows; carpet cleaners; oven cleaners; and textile and laundry pre-spotters, as well as dish detergents).

Indeed, the term "cleaning composition" as used herein, includes unless otherwise indicated, granular or powder-form all-purpose or heavy-duty washing agents, especially cleaning detergents; liquid, gel or paste-form all-purpose washing agents, especially the so-called heavy-duty liquid (HDL) types; liquid fine-fabric detergents; hand dishwashing agents or light duty dishwashing agents, especially those of the high-foaming type; machine dishwashing agents, including the various tablet, granular, liquid and rinse-aid types for household and institutional use; liquid cleaning and disinfecting agents, car or carpet shampoos, bathroom cleaners; hair shampoos and hair-rinses; shower gels and foam baths and metal cleaners; as well as cleaning auxiliaries such as bleach additives and "stain-stick" or pre-treat types.

As used herein, the terms "detergent composition" and "detergent formulation" are used in reference to mixtures which are intended for use in a wash medium for the cleaning of soiled objects. In some embodiments, the term is used in reference to laundering fabrics and/or garments (e.g., "laundry detergents"). In alternative embodiments, the term refers to other detergents, such as those used to clean dishes, cutlery, etc. (e.g., "dishwashing detergents"). It is not intended that the presently contemplated compositions be limited to any particular detergent formulation or composition. Indeed, it is intended that in addition to laccase, the term encompasses detergents that contain surfactants, transferase(s), hydrolytic enzymes, builders, bleaching agents, bleach activators, bluing agents and fluorescent dyes, caking inhibitors, masking agents, enzyme activators, antioxidants, and solubilizers.

As used herein the term "hard surface cleaning composition," refers to detergent compositions for cleaning hard surfaces such as floors, walls, tile, stainless steel vessels (e.g., fermentation tanks), bath and kitchen fixtures, and the like. Such compositions are provided in any form, including but not limited to solids, liquids, emulsions, etc.

EXAMPLES

Example 1

Expression of the Laccase D Gene in *Bacillus* as BCE103 Fusion Using Codon Optimized Synthetic Gene

```
DNA (SEQ ID NO: 5):
GGATCCTGAA GCTATCGGTC CGGTTGCAGA TTTACACATC GTAAACAAAG    50

ATCTTGCACC TGACGGCGTT CAACGTCCAA CTGTACTTGC TGGTGGAACA   100

TTCCCTGGTA CACTTATTAC TGGTCAAAAA GGTGACAACT TCCAATTAAA   150

CGTAATTGAC GATCTTACAG ATGACCGTAT GCTTACACCG ACTTCAATTC   200

ACTGGCACGG TTTCTTTCAA AAAGGAACAG CATGGGCTGA TGGTCCTGCA   250

TTCGTTACAC AATGTCCAAT CATTGCTGAT AACTCTTTCC TTTACGATTT   300

TGACGTTCCT GATCAAGCTG GTACATTCTG GTATCACTCA CACTTATCCA   350

CACAATACTG CGATGGACTT CGCGGAGCTT TCGTAGTTTA CGACCCAAAC   400

GATCCTCATA AAGACCTTTA CGATGTAGAT GATGGTGGAA CAGTTATCAC   450

ATTAGCTGAT TGGTACCATG TACTTGCTCA AACAGTTGTA GGTGCAGCTA   500

CACCAGATTC AACACTTATC AATGGATTAG GACGTTCTCA AACTGGTCCT   550
```

```
                                     -continued
GCTGACGCAG AACTTGCTGT AATCTCTGTT GAACATAACA AACGTTACAG  600

ATTCCGTCTT GTTAGCATTT CTTGCGATCC AAACTTCACA TTTTCAGTTG  650

ACGGACATAA CATGACAGTT ATCGAAGTAG ATGGTGTAAA CACACGTCCA  700

CTTACTGTAG ACTCTATCCA AATCTTCGCA GGACAACGTT ACTCATTCGT  750

ATTAAACGCA AATCAACCAG AAGATAACTA CTGGATTCGT GCAATGCCAA  800

ACATCGGACG TAACACTACA ACTCTTGACG GCAAAAACGC AGCTATTCTT  850

CGTTACAAAA ACGCTTCTGT TGAAGAACCT AAAACAGTTG GTGGACCAGC  900

ACAATCACCA CTTAACGAAG CTGACTTACG TCCACTGGTT CCAGCACCTG  950

TACCTGGAAA CGCTGTACCA GGAGGTGCTG ATATTAATCA TAGACTTAAC  100

CTTACTTTCT CTAACGGTCT GTTCTCAATC AACAACGCTT CATTCACAAA 1050

TCCTTCAGTT CCAGCACTTT TACAAATTCT TAGCGGTGCA CAAAATGCTC 1100

AGGATCTTTT ACCAACTGGA TCTTACATTG GTCTTGAACT GGGTAAAGTA 1150

GTTGAATTAG TAATTCCTCC GCTTGCTGTA GGTGGACCAC ATCCTTTCCA 1200

TCTTCACGGT CATAACTTCT GGGTTGTACG TTCTGCTGGT TCAGATGAAT 1250

ACAACTTCGA TGACGCAATT CTTCGTGATG TTGTATCTAT TGGTGCTGGA 1300

ACAGATGAAG TAACTATTCG TTTCGTAACA GATAACCCTG GTCCTTGGTT 1350

CTTACATTGT CATATCGATT GGCATCTTGA AGCTGGACTT GCTATTGTTT 1400

TCGCTGAAGG AATCAATCAA ACAGCTGCAG CTAACCCAAC ACCTCAAGCA 1450

TGGGACGAAT TATGTCCAAA ATACAACGCA CTTTCTCCAG GAGATACTTA 1500

AAAGCTT                                                1507
``` encoding the laccase D gene was synthesized by DNA2.0 Inc. (1455 Adams Drive, Menlo Park, Calif. 94025). The synthetic plasmid DNA was digested with restriction enzymes BamHI and HindIII and the 1.5 kb DNA fragment was isolated from a gel and ligated into the p2JMagk103Ink2 vector (see US20050202535A1) digested with the same two restriction enzymes to create the expression plasmid p2JMagk103Ink2E-laccase (FIG. 1). The plasmid was transformed into a B. subtilis strain (degU$^{Hy}$32, oppA, DspoIIE, DaprE, DnprE, Depr, DispA, Dbpr, Dvpr, DwprA, Dmpr-ybff, DnprB, amyE::xylRPxylAcomK-ermC) (see US20050202535A1). Two transformants were selected on Luria Broth agar plates with 5 mg/ml chloramphenicol, and then to select for clones with higher gene copy numbers, colonies were serially streaked on Luria Broth agar plates with 25 mg/ml chloramphenicol until rapid colony growth was obtained. The amplified transformants were inoculated into 30 ml MBD medium (see US20050202535A1) containing 0.5 mM copper. The cultures were grown for 60 h at 37° C. Culture broths were centrifuged and supernatants were used for ABTS assay.

Example 2

Bleaching of Solubilized Indigo with Different Laccases

An assay for the bleaching of the solubilized indigo substrate by laccase/mediator combinations was performed in a 96-well microtitre plate as follows A saturated solution of indigo in N-methylpyrrolidone (NMP) was prepared by stirring indigo (30 mg) in NMP (10 ml) at room temperature for 5 hours. The NMP solution was diluted 10-fold into an aqueous buffer solution resulting in a blue solution. For example, dilution into 50 mM sodium acetate buffer at pH 5, or 50 mM sodium phosphate buffer at pH 7. Solutions were shaken well immediately before use.

The assay for the bleaching of the solubilized indigo substrate was performed in a 96-well microtitre plate whereby each well received the soluble indigo solution in 50 mM sodium acetate buffer at pH 5 (180 uL), laccase (10 ppm enzyme) and mediator solution (from a 20 mM stock solution in methanol). The total volume of each well was adjusted to 200 uL with deionized water. A control containing laccase only was run in duplicate. The plate was sealed and incubated at 50° C. for 2 hours at 800 rpm on a heated agitator (Thermomixer, Eppendorf). Following this period, the plates were unsealed and a solution of ascorbic acid (20 uL of a 10% aqueous solution) added to each well in order to reduce the oxidized forms of the mediators. The extent of indigo bleaching was then assessed by determining the absorbance for each well at 600 nm using a microtitre plate reader. The lower the absorbance reading, the greater the extent of indigo bleaching.

FIG. 2 shows the results for a Thielavia sp. laccase (Ecostone LCC10, AB enzymes, Darmstadt, Germany). The mediators used were 2,2'-azino-bis(3-ethylbenzthiazoline-6-sulphonic acid (ABTS), syringic acid, 4-carboxamido-2,6-dimethoxyphenol (SA), methyl syringate (MS), 4-(N-methyl carboxamido)-2,6-dimethoxyphenol (MSA), 10-(carboxypropyl)-phenothiazine (PTP) and syringaldehyde. The changes in absorbance at 600 nm relative to control are listed in Table 1 where the greatest change in absorbance corresponds to the largest extent of indigo bleaching.

At a mediator concentration of 500 uM, the most effective mediator for indigo bleaching was ABTS, followed by the N-methyl amide (MSA) and the unsubstituted amide, 4-carboxamido-2,6-dimethoxyphenol (SA). At the lower mediator concentration of 50 uM, ABTS was still the most effective mediator, with the remaining mediators being more or less equivalent. The exception was syringic acid, which bleached soluble indigo no more effectively than the control condition.

TABLE 1

Change in absorbance at 600 nm following bleaching of soluble indigo using a *Thielavia* sp. laccase and a variety of mediators at 500 and 50 uM concentrations (n = 2).

| Mediator | 500 mM Concentration | | 50 mM Concentration | |
|---|---|---|---|---|
| | ΔA600 | Std Dev | ΔA600 | Std Dev |
| Control | 0 | 0.008 | 0 | 0.010 |
| ABTS | 0.235 | 0.019 | 0.174 | 0.032 |
| Syringic acid | 0.024 | 0.017 | 0.005 | 0.009 |
| SA | 0.170 | 0.018 | 0.088 | 0.014 |
| Methyl Syringate | 0.062 | 0.035 | 0.090 | 0.012 |
| MSA | 0.181 | 0.013 | 0.103 | 0.018 |
| PTP | 0.044 | 0.009 | 0.132 | 0.020 |
| Syringaldehyde | 0.132 | 0.012 | 0.092 | 0.017 |

Example 3

Soluble Indigo Bleaching Assay with Different Laccases at Two pH Values

Laccases derived from *Myceliophtora* (Denilite® II, Novozymes, Bagsvaerd, Denmark), *Thielavia* (Ecostone LCC10, AB enzymes, Darmstadt, Germany) and *Cerrena* sp. were assessed for their ability to bleach solubilized indigo in conjunction with low molecular weight mediators at two pH values.

Bleaching of solubilized indigo in 96-well microtitre plates was performed as described in Example 1, using 3 different laccases at pH values of 5 and 7. The mediators used were sinapinic acid, 4-carboxamido-2,6-dimethoxyphenol (SA), methyl 4-acetyl syringate (AMS), methyl syringate (MS) and 2,2'-azino-bis(3-ethylbenzthiazoline-6-sulphonic acid (ABTS). FIGS. 3 and 4 shows the results of soluble indigo bleaching at pH values of 5 and 7 using three laccases derived from *Myceliophtora*, *Thielavia* and *Cerrena* sp. respectively. These data are tabulated in Tables 2 and 3.

TABLE 2

Change in absorbance at 600 nm relative to a control following bleaching of soluble indigo using laccases from *Thielavia*, *Myceliophtora* and *Cerrena* sp. at pH 5, at a mediator concentration of 250 uM.

| | Laccase | | | | | |
|---|---|---|---|---|---|---|
| | *Thielavia* | | *Myceliophtora* | | *Cerrena* | |
| Mediator | ΔA$_{600}$ | Std Dev | ΔA$_{600}$ | Std Dev | ΔA$_{600}$ | Std Dev |
| Control 1 | 0 | 0.016 | 0 | 0.010 | 0 | 0.005 |
| Sinapinic acid | 0.068 | 0.019 | 0.157 | 0.020 | 0.240 | 0.007 |
| SA | 0.170 | 0.011 | 0.254 | 0.013 | 0.142 | 0.005 |
| AMS | 0.100 | 0.012 | 0.117 | 0.007 | 0.028 | 0.003 |
| MS (AB) | 0.048 | 0.011 | 0.057 | 0.007 | 0.005 | 0.011 |
| MS (Denilite) | 0.050 | 0.013 | 0.061 | 0.007 | 0.043 | 0.013 |
| ABTS | 0.234 | 0.012 | 0.267 | 0.008 | 0.329 | 0.031 |
| Control 2 | −0.007 | 0.017 | −0.011 | 0.007 | −0.006 | 0.005 |

TABLE 3

Change in absorbance at 600 nm relative to a control following bleaching of soluble indigo using laccases from *Thielavia*, *Myceliophtora* and *Cerrena* sp. at pH 7, at a mediator concentration of 250 uM.

| | Laccase | | | | | |
|---|---|---|---|---|---|---|
| | *Thielavia* | | *Myceliophtora* | | *Cerrena* | |
| Mediator | ΔA600 | Std Dev | ΔA600 | Std Dev | ΔA600 | Std Dev |
| Control 1 | 0 | 0.008 | 0 | 0.001 | 0 | 0.006 |
| Sinapinic acid | 0.112 | 0.015 | 0.204 | 0.020 | 0.257 | 0.005 |
| SA | 0.162 | 0.006 | 0.220 | 0.009 | 0.128 | 0.010 |
| AMS | 0.087 | 0.006 | 0.078 | 0.005 | 0.077 | 0.007 |
| MS (AB) | 0.053 | 0.010 | 0.076 | 0.006 | 0.000 | 0.006 |
| MS (Denilite) | 0.069 | 0.017 | 0.086 | 0.001 | 0.008 | 0.018 |
| ABTS | 0.145 | 0.006 | 0.155 | 0.014 | 0.215 | 0.056 |
| Control 2 | 0.007 | 0.006 | −0.004 | 0.001 | 0 | 0.005 |

Example 4

Bleaching of Denim Swatches with *C. unicolor* Laccase

Denim legs (made out of sulfur bottom/indigo dyed denim fabric from Cone Mill, style number 1662P) were pretreated with IndiAge® 2XL at a dose of 1 gram per liter in a 50 lb lab scale tumbling washer. The liquor ratio was 6 to 1 (5 kg substrate in 30 liters of water) and the treatment was performed at 55° C. at pH 4.5 for 1 hour. A warm rinse followed the cellulase treatment, after which the fabric was dried in a tumble dryer. A punch press was used to cut ⅝ inch denim disks from IndiAge® 2XL pretreated denim legs. Each denim disk is pre read with a Chroma Meter CR-200 by Minolta in order to determine the CIE L*a*b* values of both the front and backside of the fabric disk.

One denim disk is placed in each well of two duplicate 12 well micro-titer plates. Each well received *C. unicolor* laccase (20 uL of 1/20 dilution, approx. 20 ppm), mediator (200, 100, 50 or 20 uL of a 20 mM stock solution in methanol) and 50 mM potassium phosphate buffer, pH 6 for a total volume of 2 mL/well. The mediators were methyl syringate (MS), 4-cyano-2,6-dimethoxyphenol (SN) and 3,4,5-trimethoxyphenol (TMP). The plates were sealed and incubated at 50° C. for 2 hours at 150 rpm in a standard incubator. Following this period, the swatches were removed from the plates and carefully placed on a filter paper in a Buchner funnel and washed with copious amounts of water, followed by drying of the residual water under high vacuum overnight. The swatches were then re-read with the chromometer in order to determine the CIE L*a*b* values of both the front and backside of the disk following bleaching. The total color difference (ΔE) is calculated from the difference between the initial and final CIE L*a*b* values according to the formula $$\Delta E = (\Delta L^2 + \Delta a^2 + \Delta b^2)^{1/2}$$

The total color differences (ΔE) as a function of mediator concentration are plotted in FIGS. 5 and 6. The most effective mediator was 4-cyano-2,6-dimethoxyphenol (SN), followed by methyl syringate (MS). A dose/response relationship was seen for both compounds whereby lower concentrations of mediator gave less bleaching. The third mediator, 3,4,5-trimethoxyphenol (TMP), was not an effective mediator under these conditions. These data are tabulated in Table 4.

TABLE 4

Changes in L, a, b and total color difference (E) of both the frontside and backside of denim swatches treated with *C. unicolor* laccase (20 ppm) and 3 mediators at various concentrations.

| Mediator | | ΔL | Δa | Δb | ΔE | ΔL | Δa | Δb | ΔE |
|---|---|---|---|---|---|---|---|---|---|
| | | Denim swatch Frontside | | | | Denim swatch Backside | | | |
| MS | 2000 uM | 11.13 | −2.23 | 4.32 | 12.15 | 11.92 | −0.61 | 9.39 | 15.19 |
| | | 12.46 | −2.35 | 4.76 | 13.54 | 12.01 | −0.42 | 9.88 | 15.56 |
| | 1000 uM | 11.55 | −2.53 | 3.27 | 12.27 | 8.42 | −0.12 | 6.4 | 10.58 |
| | | 9.58 | −2.23 | 3.03 | 10.29 | 9.22 | −0.49 | 7.0 | 11.59 |
| | 500 uM | 6.5 | −1.18 | 1.65 | 6.81 | 7.53 | 0.09 | 5.68 | 9.43 |
| | | 8.22 | −1.48 | 2.38 | 8.68 | 8.54 | −0.23 | 5.75 | 10.30 |
| | 200 uM | 4.67 | −0.99 | 1.25 | 4.93 | 5.83 | 0.14 | 4.35 | 7.28 |
| | | 5.29 | −0.94 | 1.1 | 5.48 | 6.36 | 0.06 | 4.34 | 7.70 |
| SN | 2000 uM | 14.79 | −2.11 | 5.8 | 16.03 | 12.34 | 0.01 | 9.06 | 15.31 |
| | | 13.23 | −1.87 | 5.58 | 14.48 | 13.58 | −0.37 | 9.52 | 16.59 |
| | 1000 uM | 13.54 | −2.05 | 5.47 | 14.75 | 11.45 | 0.07 | 8.02 | 13.98 |
| | | 13.84 | −2.49 | 4.98 | 14.92 | 12.1 | 0.14 | 9.19 | 15.19 |
| | 500 uM | 14.46 | −1.9 | 5.51 | 15.59 | 10.71 | 0.35 | 8.1 | 13.43 |
| | | 12.06 | −1.97 | 4.92 | 13.17 | 11.6 | 0.38 | 8.03 | 14.11 |
| | 200 uM | 6.63 | −1.35 | 2.57 | 7.24 | 8.38 | 0.54 | 6.12 | 10.39 |
| | | 7.98 | −1.28 | 2.67 | 8.51 | 8.67 | 0.38 | 5.67 | 10.37 |
| TMP | 2000 uM | −0.06 | 0.15 | 0.1 | 0.19 | 0.26 | −0.12 | 0.19 | 0.34 |
| | | −0.23 | 0.05 | −0.32 | 0.40 | −0.3 | 0.06 | −0.14 | 0.34 |
| | 1000 uM | 0.47 | −0.2 | 0.04 | 0.51 | 0.36 | 0.22 | 0.15 | 0.45 |
| | | −0.07 | 0.18 | −0.42 | 0.46 | −0.49 | 0.12 | −0.07 | 0.51 |
| | 500 uM | −0.61 | −0.06 | 0.18 | 0.64 | −0.43 | 0.2 | −0.19 | 0.51 |
| | | −0.61 | 0.14 | −0.06 | 0.63 | 0.29 | 0.09 | −0.01 | 0.30 |
| | 200 uM | −0.91 | 0.29 | 0.01 | 0.96 | −0.1 | −0.14 | 0.3 | 0.35 |
| | | −0.68 | 0.33 | −0.12 | 0.77 | −0.49 | 0.14 | −0.26 | 0.57 |

[1]MS—methyl syringate, SN = 4-cyano-2,6-dimethoxyphenol, TMP = 3,4,5-trimethoxyphenol.
[2]Difference in L, a and b values was determined by subtracting initial from final readings.

Example 5

Bleaching of Denim Swatches with Recombinant *C. unicolor* Laccase D

A denim swatch bleaching assay was performed as described in Example 16, in this instance, using a recombinant form of the laccase D protein derived from *C. unicolor*. Two duplicate 12-well plates were loaded with denim disks. The laccase D stock solution (5.5 ABTS units per mL) was dosed at either 25 or 50 uL per well. The mediators used were methyl syringate (MS), 4-cyano-2,6-dimethoxyphenol (SN) and 4-carboxamido-2,6-dimethoxyphenol (SA) and were used at either 0.5 or 1 mM concentration. The results are depicted in FIGS. 7 and 8. The changes in L, a, b values and the corresponding total color differences (ΔE) are listed in Table 5. The results indicate that 4-cyano-2,6-dimethoxyphenol (SN) was the most effective mediator for swatch bleaching under these conditions.

TABLE 5

Total color differences for bleached denim disks as a function of laccase/mediator combinations using laccase D from *C. unicolor*.

| Conditions | | | Denim swatch Frontside | | | | Denim swatch Backside | | | |
|---|---|---|---|---|---|---|---|---|---|---|
| Mediator[1] | | Laccase[2] | ΔL | Δa | Δb | ΔE | ΔL | Δa | Δb | ΔE |
| MS | 1 mM | 50 uL | 11.77 | −2.20 | 4.67 | 12.85 | 11.16 | 0.34 | 8.52 | 14.04 |
| | | | 11.57 | −2.15 | 4.51 | 12.60 | 10.30 | 0.50 | 8.26 | 13.21 |
| MS | 0.5 mM | 50 uL | 7.74 | −1.92 | 2.45 | 8.34 | 7.93 | 0.33 | 6.29 | 10.13 |
| | | | 7.12 | −1.70 | 2.21 | 7.65 | 8.34 | 0.17 | 6.47 | 10.56 |
| MS | 1 mM | 25 uL | 10.74 | −1.90 | 4.82 | 11.92 | 9.44 | 0.16 | 7.99 | 12.37 |
| | | | 11.15 | −2.46 | 3.93 | 12.08 | 10.25 | 0.26 | 7.89 | 12.94 |
| MS | 0.5 mM | 25 uL | 8.55 | −1.90 | 3.12 | 9.30 | 9.35 | 0.00 | 6.36 | 11.31 |
| | | | 9.53 | −1.91 | 3.43 | 10.31 | 9.10 | 0.03 | 6.70 | 11.30 |
| SN | 1 mM | 50 uL | 12.98 | −2.04 | 5.33 | 14.18 | 11.25 | 0.29 | 8.41 | 14.05 |
| | | | 12.85 | −2.23 | 5.50 | 14.15 | 10.98 | 0.48 | 8.91 | 14.15 |
| SN | 0.5 mM | 50 uL | 8.20 | −1.70 | 2.34 | 8.70 | 8.87 | 0.26 | 5.93 | 10.67 |
| | | | 8.67 | −1.76 | 2.90 | 9.31 | 8.45 | 0.33 | 6.19 | 10.48 |
| SN | 1 mM | 25 uL | 12.31 | −2.17 | 4.36 | 13.24 | 11.36 | 0.01 | 7.93 | 13.85 |
| | | | 12.85 | −2.02 | 4.85 | 13.88 | 10.64 | 0.13 | 7.59 | 13.07 |
| SN | 0.5 mM | 25 uL | 9.23 | −2.17 | 3.12 | 9.98 | 9.69 | −0.15 | 6.41 | 11.62 |
| | | | 9.73 | −1.91 | 3.39 | 10.48 | 9.31 | 0.36 | 6.81 | 11.54 |
| SA | 1 mM | 50 uL | 6.23 | −1.83 | 1.73 | 6.72 | 6.52 | 0.15 | 5.79 | 8.72 |
| | | | 7.37 | −2.01 | 2.11 | 7.93 | 6.82 | 0.10 | 6.12 | 9.16 |
| SA | 0.5 mM | 50 uL | 3.66 | −1.23 | 0.87 | 3.96 | 4.64 | −0.10 | 4.04 | 6.15 |
| | | | 4.46 | −1.38 | 0.88 | 4.75 | 5.25 | −0.19 | 4.17 | 6.71 |

TABLE 5-continued

Total color differences for bleached denim disks as a function of laccase/mediator combinations using laccase D from C. unicolor.

| Conditions | | Denim swatch Frontside | | | | Denim swatch Backside | | | |
|---|---|---|---|---|---|---|---|---|---|
| Mediator[1] | Laccase[2] | ΔL | Δa | Δb | ΔE | ΔL | Δa | Δb | ΔE |
| SA | 1 mM | 25 uL | 7.07 | −1.97 | 1.76 | 7.55 | 7.02 | 0.09 | 5.51 | 8.92 |
| | | | 7.19 | −2.18 | 1.68 | 7.70 | 6.53 | −0.45 | 5.22 | 8.37 |
| SA | 0.5 mM | 25 uL | 4.73 | −1.41 | 1.16 | 5.07 | 4.94 | −0.16 | 4.51 | 6.69 |
| | | | 5.28 | −1.56 | 1.47 | 5.70 | 4.93 | −0.33 | 4.05 | 6.39 |

[1]MS = Methyl syringate, SN = 4-cyano-2,6-dimethoxyphenol, SA = 4-carboxamido-2,6-dimethoxyphenol.
[2]Laccase stock was a concentrate with an activity of 5.5 U/mL against ABTS.

Example 6

Stability of Mediators in the Presence of C. unicolor Laccase

Aliquots of supernatant were analyzed by LC/MS following the denim disk bleaching protocol described in Example 5 in order to determine the final mediator concentrations in the supernatant following the 2 hour incubation period.

Standard solutions of the mediators were prepared by dilution of the methanolic stock solutions (20 mM) into deionized water, such that the final concentrations were 1 mM respectively for each of the three mediators methyl syringate (MS), 4-cyano-2,6-dimethoxyphenol (SN) and, 4-carboxamido-2,6-dimethoxyphenol (SA). Samples were analyzed using a Thermo Finnegan Quantum TSQ LC/MS system (Thermo Finnegan, San Jose, Calif.) operating in positive electrospray ionization mode. The liquid chromatography conditions were as follows:

Column; Agilent Zorbax SB-Aq, 2.1 mm×100 mm, 3.5 uM silica
Solvent A; 20 mM Ammonium formate, pH 5.0
Solvent B; 90% Methanol+10% solvent A
Flow rate; 250 uL/min
Injection volume; 5 uL
Elution program; 70% solvent A from 0 to 1 minute, to 30% A from 3 to 4 minutes, back to 70% A at 4.5 minutes, held at 70% A until 8 minutes overall.

The Mass spectrometry conditions were as follows:
Positive mode electrospray ionization (+ve ESI) in full scan mode, scanning from 175 to 240 Da in 0.5 seconds. Spray voltage was 4200V, sheath gas flow rate 41 mL/min, aux gas flow rate at 15 mL/min. Tube lens voltage was 109V and capillary temperature was 270° C.

The results of the experiment are shown in Table 6.

TABLE 6

Stability of mediators as determined by initial and final concentrations in the supernatant used to bleach denim disks.

| Mediator | Initial Peak Area | Final Peak Area | % Remaining |
|---|---|---|---|
| MS | 133 × 10$^7$ | 40.2 × 10$^7$ | 30.2% |
| SN | 35.6 × 10$^7$ | 35.2 × 10$^7$ | 98.9% |
| SA | 122 × 10$^7$ | 0.94 × 10$^7$ | 7.8% |

[1]MS = Methyl syringate, SN = 4-cyano-2,6-dimethoxyphenol, SA = 4-carboxamido-2,6-dimethoxyphenol.

The results indicate that the stability of the mediators differs widely upon contact with laccase and substrate for the standard incubation conditions of 2 hours at 50° C. In this instance 4-cyano-2,6-dimethoxyphenol (SN) was by far the most stable compound, the concentration of which was essentially unchanged (98.9% remained), followed by methyl syringate (30.2% remained). The least stable mediator compound was 4-carboxamido-2,6-dimethoxyphenol (SA), with only 7.8% remaining at the endpoint of the experiment.

Example 7

Purification and Determination of Specific Activity

The laccase D optimized gene (see SEQ ID NO: 70 of U.S. Pat. No. 8,105,812 was expressed using the expression system described in co-pending application U.S. 60/984,430 entitled "Signal Sequences and co-expressed chaperones for improved heterologous protein production in a host cell" filed 1 Nov. 2007) in 14 liter fermenters. Fermentation broth from was harvested at 184 hours and concentrated by ultra filtration (UFC 20070245). The concentrate was diafiltered into 25 mM sodium acetate, pH4.0 buffer. Then 500 ml of the diafiltered UFC sample was loaded on to an ion exchange column containing Poros HS-20 resin (Applied Biosystems, 20×275 mm column) equilibrated with 25 mM sodium acetate buffer, pH 4.0. The column was washed with 10 column volumes of 25 mM sodium acetate buffer, pH 4.0. The laccase D protein was eluted from the column using a salt gradient (12 column volumes) from 40 mm to 80 mM sodium chloride in 25 mM sodium acetate buffer, pH 4.0. Fractions containing laccase activity were pooled and further concentrated using an Amicon 400 mL stir cell with a 10K membrane. Total protein was measure by SDS protein gel using BSA as standard as 4 mg/ml (>90% pure). The laccase sample was diluted 10,000 fold with water and stored at RT for 18 hours and at 4° C. for more than 24 hours. ABTS activity was measured as 8570 units/ml. The specific activity of the recombinant laccase D is then calculated by dividing 8570 units/ml by 4 mg/ml resulting in 2140 units/mg of protein which is 100 times more activity than the Stachybotrys laccase (16 u/mg), see Mander et al, Appl. Environ. Microbiol. (2006) 72:5020-5026). Thus, this enzyme results in lower copper discharge into the environment than other laccases, e.g., Stachybotrys laccase, by virtue of the high specific activity.

Example 8

Procedure for Denim Bleaching

Mediators 4-hydroxy-3,5-dimethoxybenzamide (syringamide, SA) was purchased from Punjab Chemicals & Crop Protection Limited (Mumbai, India). 4-hydroxy-3,5-dimethoxybenzonitrile (syringonitrile, SN) was acquired from StereoChemical, Inc., (Newark, Del.) or Punjab Chemicals & Crop Protection Limited (Mumbai, India).

Enzyme

Laccase enzyme, derived from *Cerrena unicolor* (Example 7, 8570 U/ml, 4 mg protein/ml) was used in the experiments.

Procedure

The enzyme incubations were done in an ATLAS LP 2 Launder-O-meter at different conditions in relation to pH, temperature, enzyme concentration and mediator concentration.

Reactions were carried out in 500 ml stainless steel reaction vessels containing 100 ml of liquid. To each vessel five (7×7 cm) stonewashed denim swatches (ACG denim style 80270) and 6 steel balls of 6 mm diameter were added. The reactions vessels were closed and entered into the launder-O-meter that was pre-heated to the desired temperature. The incubation was carried out for 30 minutes after which the swatches were washed with 'running' tap water, spin dried in an AEG IPX4 centrifuge and dried with an Elna Press Electronic iron at program cotton and evaluated.

Stonewashing of Denim

Denim, 12 legs weighing approximately 3 kg, was desized in a Unimac UF 50 washing machine under the following conditions:

Desizing for 15 minutes at 10:1 liquor ratio 50° C. with 0.5 g/l (15 g) of Optisize 160 amylase (Genencor) and 0.5 g/l (15 g) of a non-ionic surfactant (e.g. Rucogen BFA, (Rudolf Chemie) or Ultravon GPN, (Huntsman))

2 cold rinses for 5 minutes at 30:1 liquor ratio.

Following desizing the denim was stonewashed in a Unimac UF 50 washing machine under the following conditions:

Cold rinse for 5 minutes at 10:1 liquor ratio

Stonewashing for 60 minutes at 10:1 liquor ratio 55° C. with 1 kg of pumice stone, citrate buffer (30 g tri-sodium citrate dihydrate and 30 g citric acid monohydrate) and 35 g IndiAge 2XL cellulase (Genencor).

2 cold rinses for 5 minutes at 30:1 liquor ratio.

The denim was dried in a Miele Novotronic T494C household fabric dryer. From the denim legs, swatches of 7×7 cm were cut.

Evaluation of Denim Swatches

The color of the five denim swatches is measured with a Minolta Chromameter CR 310 in the CIE Lab color space with a D 65 light source. Measurements were done before and after laccase treatment and the results of the five swatches were averaged. The total color difference (TCD) is calculated. The total color difference can be calculated with the formula: $TCD=\sqrt{(\Delta L)^2+(\Delta a)^2+(\Delta b)^2}$.

Evaluation of Denim Legs

Denim legs were evaluated with a Minolta Chromameter CR 310 in the CIE Lab color space with a D 65 light source. Measurements were done only after laccase treatment. For each denim leg 8 measurements are taken and the result of the 12 legs (96 measurements) was averaged.

Example 9

Effect of Temperature on the Recombinant Laccase D Bleaching Performance (Unimac)

Laccase bleaching of stonewashed denim: Denim, 12 legs approximately 3 kg, was desized and stonewashed as described in example 8. After stonewashing a laccase treatment was done in a Unimac UF 50 washing machine according to the following process:

30 minutes at 10:1 liquor ratio, pH 6 (21 g monosodium phosphate and 5 g adipic acid, recombinant laccase D) or pH 4.8 (8.6 g monosodium phosphate and 16.8 g of adipic acid, Novoprime Base 268 laccase)

laccase (recombinant laccase D or Novoprime Base 268)

mediator (syringamide (SA) and syringonitrile (SN))

After laccase treatment the denim use rinsed twice in cold water for 5 minutes at 30:1 liquor ratio.

The laccase experiments were carried out and the results are presented in Tables 7 and 8.

TABLE 7

| *Cerrena unicolor* Laccase concentration | Mediator | Mediator concentration | Temperature (° C.) | Bleaching level (CIE L) |
|---|---|---|---|---|
| 0.05 g/l/0.4 U/ml | SA | 0.33 mM | 60 | 35.6 |
| 0.05 g/l/0.4 U/ml | SN | 0.47 mM | 60 | 35.9 |
| 0.05 g/l/0.4 U/ml | SA | 0.33 mM | 40 | 35.6 |
| 0.05 g/l/0.4 U/ml | SN | 0.47 mM | 40 | 35.7 |

TABLE 8

| Novoprime base 268 concentration | Mediator concentration | Temperature (° C.) | Bleaching level (CIE L) |
|---|---|---|---|
| 0.05 g/l | 0.023 g/l | 60 | 35.9 |
| 0.05 g/l | 0.023 g/l | 40 | 33.7 |

The recombinant laccase D has better performance at lower temperatures than currently available commercial laccases. The laccase (in the presence of mediator) provides a bleaching effect at temperatures below 60° C., preferably between 40° C. and 60° C. Thus, the laccase may provide an energy benefit to the textile processor.

Example 10

Effect of Recombinant Laccase D Enzyme and Mediator Concentration on Bleaching Performance (Launder-O-Meter)

The effect of laccase and mediator concentration was evaluated running the experiments in the tables below at pH 6 (50 mM monosodium phosphate buffer pH adjusted with sodium hydroxide 4N solution) and a temperature of 60° C.

The experiments were done with syringamide (SA)- and syringonitrile (SN) mediator.

100 ml buffer was added to a beaker with five swatches, 7×7 cm. The total weight 12 g, (denim:liquor ratio=1:8). Laccase and mediator concentrations were used as indicated in the tables below.

TABLE 9

| Laccase enzyme concentration (µl/l) | Activity correspondence (Laccase unit/g denim) |
|---|---|
| 10 | 0.67 |
| 33 | 2.17 |
| 55 | 3.67 |
| 78 | 5.17 |
| 100 | 6.67 |

TABLE 10

| Mediator Concentration (mM) |
|---|
| 0.10 |
| 0.33 |
| 0.55 |
| 0.78 |
| 1.00 |

The amounts of syringamide or syringonitrile mediator as indicated in the tables below were added to each beaker as a dilution of a 275 mM SA—or—SN stock solution in 98% methanol. The laccase was added to each beaker as indicated in the tables below, as dilution of a 400 units/ml laccase stock solution. The beakers were closed and processed at 60° C. as described in the example 8. The swatches were evaluated as described in example 8.

TABLE 11

LACCASE + SA at 60° C. pH 6

| Laccase (µl/l) | Mediator syringamide (mM) | TCD |
|---|---|---|
| 100 | 1.00 | 5.6 |
| 100 | 1.00 | 6.0 |
| 100 | 0.10 | 2.9 |
| 78 | 0.33 | 4.4 |
| 55 | 1.00 | 6.2 |
| 55 | 0.55 | 5.3 |
| 33 | 0.78 | 5.5 |
| 33 | 0.33 | 4.6 |
| 10 | 1.00 | 3.2 |
| 10 | 0.10 | 2.5 |
| 55 | 0.55 | 5.8 |
| 100 | 0.55 | 5.3 |
| 78 | 0.78 | 5.9 |
| 100 | 0.10 | 3.2 |
| 55 | 0.10 | 3.1 |
| 10 | 0.55 | 3.6 |

TCD = total color difference

TABLE 12

LACCASE + SN at 60° C. pH 6

| Laccase (µl/l) | Mediator syringonitrile (mM) | TCD |
|---|---|---|
| 100 | 1.00 | 7.6 |
| 100 | 1.00 | 8.1 |
| 100 | 0.10 | 4.1 |
| 78 | 0.33 | 5.6 |
| 55 | 1.00 | 7.0 |
| 55 | 0.55 | 6.0 |
| 33 | 0.78 | 5.5 |
| 33 | 0.33 | 4.4 |
| 10 | 1.00 | 3.8 |
| 10 | 0.10 | 2.7 |
| 55 | 0.55 | 6.3 |
| 100 | 0.55 | 7.1 |
| 78 | 0.78 | 7.1 |
| 100 | 0.10 | 4.0 |
| 55 | 0.10 | 3.5 |
| 10 | 0.55 | 3.4 |

TCD = total color difference

Figure 9:
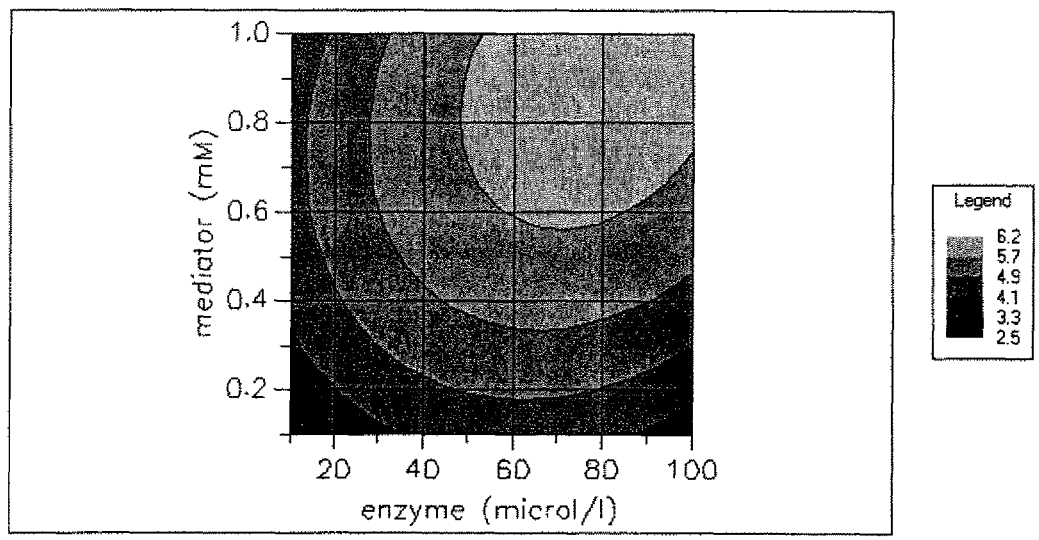
FIG. 9 is a total color difference graph for the recombinant laccase D and syringamide mediator as a function of mediator concentration and enzyme concentration at 60° C. and pH 6.
Figure 10:
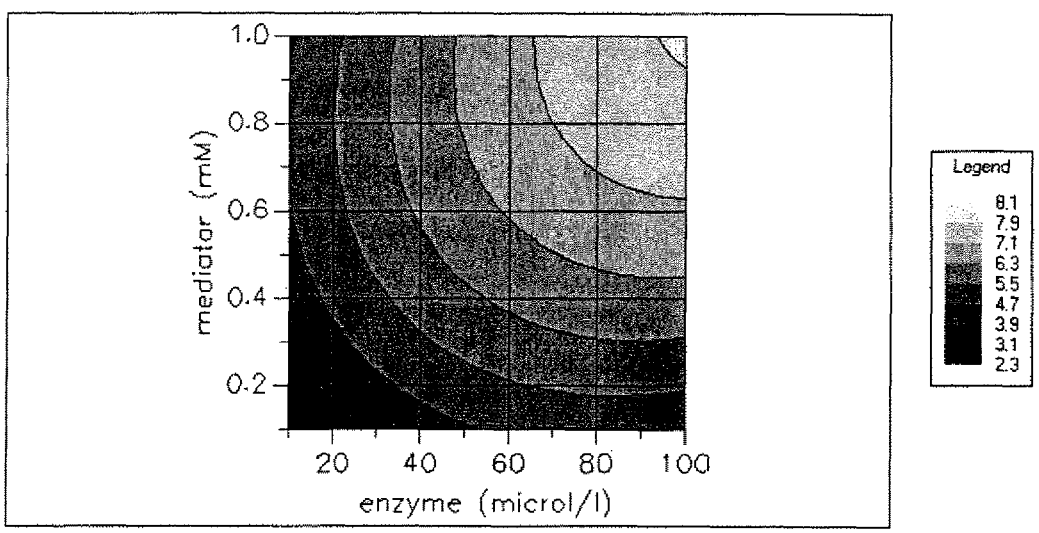
FIG. 10 is a total color difference graph for the recombinant laccase D and syringonitrile mediator as a function of mediator concentration and enzyme concentration at 60° C. and pH 6.

The above Tables and FIGS. 9 and 10 show that you need both enzyme and mediator to get bleaching. Also it shows there is some flexibility in the enzyme/mediator ratio in achieving a certain bleaching level.

Example 11

Recombinant Laccase D Dose Response Effect on the Bleaching Performance (Unimac)

Laccase bleaching of stonewashed denim—Denim, 12 legs weighing approximately 3 kg, was desized and stonewashed as described in Example 8. After stonewashing, a laccase treatment was done according to the following process: 30 minutes at 10:1 liquor ratio and pH 6 (21 g monosodium phosphate and 5 g adipic acid) and 60° C. with laccase and mediator. After laccase treatment the denim use rinsed twice in cold water for 5 minutes at 30:1 liquor ratio.

The following experiments were carried out.

Syringamide 0.33 mM:

| Cerrena unicolor laccase concentration (g/l) | Bleaching level (CIE L) |
|---|---|
| 0.010 | 34.6 |
| 0.05 | 36.2 |
| 0.25 | 36.2 |

Syringonitrile 0.39 mM:

| Cerrena unicolor laccase concentration (g/l) | Bleaching level (CIE L) |
|---|---|
| 0.25 | 37.7 |
| 0.4 | 39.5 |
| 0.53 | 38.8 |

The results are shown in the above tables. This shows that with recombinant laccase D and the amide mediator the bleaching level flattens quite quickly. With an enzyme concentration of 0.05 and 0.25 the same bleaching level is obtained. For the recombinant laccase D and the nitrile mediator the bleaching level increases up to 0.4 g/l, where there appears to be an optimum.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety.

The invention claimed is:

1. A process for providing a bleached look in the colour density of the surface of dyed fabric, the process comprising contacting, in an aqueous medium, a dyed fabric with a phenol oxidizing enzyme system and an enhancing agent of the following formula:

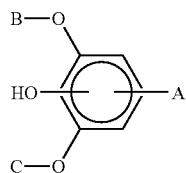

wherein A is —CN; and B and C may be the same or different and selected from $C_mH_{2m+1}$, $1 \leq m \leq 5$.

2. The process according to claim 1, wherein the fabric is dyed with a vat dye.

3. The process according to claim 1, wherein the fabric is a cellulosic fabric or a mixture of cellulosic fibres or a mixture of cellulosic fibres and synthetic fibres.

4. The process according to claim 1, wherein the fabric is denim.

5. The process according to claim 1, in which the phenol oxidizing enzyme system is selected from a peroxidase and a hydrogen peroxide source.

6. The process according to claim 5, wherein the peroxidase is horseradish peroxidase, soybean peroxidase, or a peroxidase enzyme derived from *Coprinus, Bacillus,* or *Myxococcus*.

7. The process according to claim 5, wherein the hydrogen peroxide source is hydrogen peroxide or a hydrogen peroxide precursor, a hydrogen peroxide generating enzyme system, or a peroxycarboxylic acid or a salt thereof.

8. The process according to claim 1, wherein the aqueous medium contains $H_2O_2$ or a precursor for $H_2O_2$ in a concentration corresponding to 0.001-25 mM $H_2O_2$.

9. The process according to claim 1, wherein the phenol oxidizing enzyme system is a laccase or a laccase related enzyme together with oxygen.

10. The process according to claim 9, wherein the laccase is derived from *Aspergillus, Neurospora, Podospora, Botrytis, Collybia, Cerrena, Stachybotrys, Panus, Theilava, Fomes, Lentinus, Pleurotus, Trametes, Rhizoctonia, Coprinus, Psatyrella, Myceliophthora, Schytalidium, Phlebia, Coriolus, Spongipellis, Polyporus, Ceriporiopsis, Ganoderma,* or *Trichoderma*.

11. The process according to claim 1, wherein the fabric is denim and the concentration of the phenol oxidizing enzyme corresponds to 0.001-10000 μg of enzyme protein per g of denim.

12. The process according to claim 1, wherein the fabric is denim and the enhancing agent in the aqueous medium is present in concentrations of from 0.005 to 1000 μmole per g denim.

13. The process according to claim 1, wherein the enhancing agent is

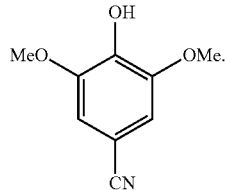

4-Cyano-2,6-dimethoxyphenol

14. The process according to claim 10, wherein the laccase is derived from a *Cerrena* spp.

15. The process according to claim 14, wherein the laccase is derived from *Cerrena unicolor*.

16. The process according to claim 15, wherein the laccase is *Cerrena unicolor* laccase D.

17. The process according to claim 6, wherein the enzyme is derived from *C. cinereus, C. macrorhizus, B. pumilus,* or *M. virescens*.

18. The process according to claim 7, wherein the hydrogen peroxide precursor is perborate or percarbonate, and the hydrogen peroxide generating enzyme system is an oxidase and its substrate.

19. The process according to claim 10, wherein the laccase is derived from *Neurospora crassa, Panus rudis, Trametes villosa, Trametes versicolor, Rhizoctonia solani, Coprinus plicatilis, Coprinus cinereus, Myceliophthora thermonhila, Phlebia radita, Coriolus hirsutus, Ceriporiopsis subvermispora, Ganoderma tsunodae,* or *Trichoderma reesie*.

20. The process according to claim 2, wherein the vat dye is indigo or thioindigo.

21. The process according to claim 4, wherein the fabric is denim dyed with indigo or thioindigo.

22. The process according to claim 1, wherein the enhancing agent is syringonitrile.

* * * * *

SEQUENCE LISTING

<160> NUMBER OF SEQ ID NOS: 5

<210> SEQ ID NO 1
<211> LENGTH: 2809

<212> TYPE: DNA
<213> ORGANISM: Cerrena unicolor

<400> SEQUENCE: 1

| | | | | | |
|---|---|---|---|---|---|
| gattctaata | gaccaggcat | accaagagat | ctacaggttg | acagaccatt | cttctaggcg | 60 |
| gcatttatgc | tgtagcgtca | gaaattatct | ctccatttgt | atcccacagg | tcctgtaata | 120 |
| acacggagac | agtccaaact | gggatgcctt | ttttctcaac | tatgggcgca | catagtctgg | 180 |
| acgatggtat | ataagacgat | ggtatgagac | ccatgaagtc | agaacacttt | tgctctctga | 240 |
| catttcatgg | ttcacactct | cgagatggga | ttgaactcgg | ctattacatc | gcttgctatc | 300 |
| ttagctctgt | cagtcggaag | ctatgctgca | attgggcccg | tggccgacat | acacattgtc | 360 |
| aacaaagacc | ttgctccaga | tggcgtacaa | cgtccaaccg | tgcttgccgg | aggcactttt | 420 |
| cctgggacgt | tgatcaccgg | tcagaaagta | agggatatta | gtttgcgtca | aagagccaac | 480 |
| caaaactaac | cgtcccgtac | tatagggtga | caacttccag | ctcaatgtca | tcgatgatct | 540 |
| taccgacgat | cggatgttga | cgccaacttc | cattgtgagc | ctattattgt | atgatttatc | 600 |
| cgaatagttt | cgcagtctga | tcattggatc | tctatcgcta | gcattggcac | ggtttcttcc | 660 |
| agaagggaac | cgcttgggcc | gacggtcccg | ccttcgtaac | tcagtgccct | ataatagcag | 720 |
| ataactcttt | tctgtatgac | ttcgacgtcc | cagaccaagc | tggtactttc | tggtatcata | 780 |
| gtcatctatc | cactcagtac | tgtgacggtt | tacgtggtgc | cttcgttgtg | tacgatccta | 840 |
| acgatcctca | caaagaccta | tacgatgttg | atgacggtgg | gttccaaata | tttgttctgc | 900 |
| agacattgta | ttgacggtgt | tcattataat | ttcagagagc | accgtgatta | cccttgcgga | 960 |
| ttggtaccat | gttctcgccc | agaccgttgt | cggcgctgcg | tgagtaacac | atacacgcgc | 1020 |
| tccggcacac | tgatactaat | tttttttat | tgtagcactc | ctgattctac | cttgatcaac | 1080 |
| gggttaggcc | gttcacagac | cggacccgct | gatgctgagc | tggctgttat | cagcgttgaa | 1140 |
| cataacaaac | ggtatgtcat | ctctacccag | tatcttctct | cctgctctaa | ttcgctgttt | 1200 |
| caccatagat | accgtttccg | tttggtttcg | atttcgtgcg | accccaactt | taccttctcc | 1260 |
| gttgatggtc | ataatatgac | tgtcatcgaa | gtcgatggtg | tcaacacacg | acccctgacc | 1320 |
| gttgactcta | ttcaaatctt | cgccggacag | aggtattcct | ttgtcgtaag | ttaatcgata | 1380 |
| tattctcctt | attaccctg | tgtaattgat | gtcaatagct | caatgctaac | caacccgaag | 1440 |
| acaattactg | gatccgtgct | atgccaaaca | tcggtagaaa | tacaacaaca | ctggacggaa | 1500 |
| agaatgccgc | tatccttcga | tacaagaatg | cttctgtaga | agagcccaag | accgttgggg | 1560 |
| gccccgctca | atcccgttg | aatgaagcgg | acctgcgtcc | actcgtacct | gctcctgtgg | 1620 |
| tatgtcttgt | cgcgctgttc | catcgctatt | tcatattaac | gttttgtttt | tgtcaagcct | 1680 |
| ggaaacgctg | ttccaggtgg | cgcagacatc | aatcacaggc | ttaacttaac | tttcgtacgt | 1740 |
| acacctggtt | gaaacattat | atttccagtc | taacctctct | tgtagagtaa | cggcctcttc | 1800 |
| agcatcaaca | acgcctcctt | cactaatcct | tcggtccccg | ccttattaca | aattctgagc | 1860 |
| ggtgctcaga | acgctcaaga | tttacttcca | acgggtagtt | acattggcct | tgaactaggc | 1920 |
| aaggttgtgg | agctcgttat | acctcctctg | gcagttggag | gaccgcaccc | tttccatctt | 1980 |
| catggcgtaa | gcataccaca | ctcccgcagc | cagaatgacg | caaactaatc | atgatatgca | 2040 |
| gcacaatttc | tgggtcgtcc | gtagtgcagg | tagcgatgag | tataactttg | acgatgctat | 2100 |
| cctcagggac | gtcgtragca | ttggagcggg | gactgatgaa | gtcacaatcc | gtttcgtggt | 2160 |
| atgtctcacc | cctcgcattt | tgagacgcaa | gagctgatat | attttaacat | agaccgacaa | 2220 |
| tccgggcccg | tggttcctcc | attgccatat | tgattggcat | ttggaggcag | gccttgccat | 2280 |

-continued

```
cgtcttcgct gagggcatca atcagaccgc tgcagccaac ccaacacccc gtacgtgaca    2340
ctgagggttt ctttatagtg ctggattact gaatcgagat ttctccacag aagcatggga    2400
tgagctttgc cccaaatata acgggttgag tgcgagccag aaggtcaagc taagaaagg     2460 aactgctatt taaacgtggt cctagactac gggcatataa gtattcgggt agcgcgtgtg    2520
agcaatgttc cgatacacgt agattcatca ccggacacgc tgggacaatt tgtgtataat    2580
ggctagtaac gtatctgagt tctggtgtgt agttcaaaga gacagccctt cctgagacag    2640
cccttcctga gacagccctt cctgagacgt gacctccgta gtctgcacac gatactycta    2700
aatacgtatg gcaagatgac aaagaggagg atgtgagtta ctacgaacag aaatagtgcc    2760
cggcctcgga gagatgttct tgaatatggg actgggacca acatccgga              2809
```

<210> SEQ ID NO 2
<211> LENGTH: 526
<212> TYPE: PRT
<213> ORGANISM: Cerrena unicolor

<400> SEQUENCE: 2

```
Met Gly Leu Asn Ser Ala Ile Thr Ser Leu Ala Ile Leu Ala Leu Ser
 1               5                  10                  15

Val Gly Ser Tyr Ala Ala Ile Gly Pro Val Ala Asp Ile His Ile Val
            20                  25                  30

Asn Lys Asp Leu Ala Pro Asp Gly Val Gln Arg Pro Thr Val Leu Ala
        35                  40                  45

Gly Gly Thr Phe Pro Gly Thr Leu Ile Thr Gly Gln Lys Gly Asp Asn
    50                  55                  60

Phe Gln Leu Asn Val Ile Asp Asp Leu Thr Asp Asp Arg Met Leu Thr
65                  70                  75                  80

Pro Thr Ser Ile His Trp His Gly Phe Phe Gln Lys Gly Thr Ala Trp
                85                  90                  95

Ala Asp Gly Pro Ala Phe Val Thr Gln Cys Pro Ile Ile Ala Asp Asn
            100                 105                 110

Ser Phe Leu Tyr Asp Phe Asp Val Pro Asp Gln Ala Gly Thr Phe Trp
        115                 120                 125

Tyr His Ser His Leu Ser Thr Gln Tyr Cys Asp Gly Leu Arg Gly Ala
    130                 135                 140

Phe Val Val Tyr Asp Pro Asn Asp Pro His Lys Asp Leu Tyr Asp Val
145                 150                 155                 160

Asp Asp Gly Gly Thr Val Ile Thr Leu Ala Asp Trp Tyr His Val Leu
                165                 170                 175

Ala Gln Thr Val Val Gly Ala Ala Thr Pro Asp Ser Thr Leu Ile Asn
            180                 185                 190

Gly Leu Gly Arg Ser Gln Thr Gly Pro Ala Asp Ala Glu Leu Ala Val
        195                 200                 205

Ile Ser Val Glu His Asn Lys Arg Tyr Arg Phe Arg Leu Val Ser Ile
    210                 215                 220

Ser Cys Asp Pro Asn Phe Thr Phe Ser Val Asp Gly His Asn Met Thr
225                 230                 235                 240

Val Ile Glu Val Asp Gly Val Asn Thr Arg Pro Leu Thr Val Asp Ser
                245                 250                 255

Ile Gln Ile Phe Ala Gly Gln Arg Tyr Ser Phe Val Leu Asn Ala Asn
            260                 265                 270

Gln Pro Glu Asp Asn Tyr Trp Ile Arg Ala Met Pro Asn Ile Gly Arg
        275                 280                 285
```

```
Asn Thr Thr Thr Leu Asp Gly Lys Asn Ala Ala Ile Leu Arg Tyr Lys
    290                 295                 300
Asn Ala Ser Val Glu Glu Pro Lys Thr Val Gly Pro Ala Gln Ser
305                 310                 315                 320
Pro Leu Asn Glu Ala Asp Leu Arg Pro Leu Val Pro Ala Pro Val Pro
                325                 330                 335
Gly Asn Ala Val Pro Gly Gly Ala Asp Ile Asn His Arg Leu Asn Leu
            340                 345                 350
Thr Phe Ser Asn Gly Leu Phe Ser Ile Asn Asn Ala Ser Phe Thr Asn
        355                 360                 365
Pro Ser Val Pro Ala Leu Leu Gln Ile Leu Ser Gly Ala Gln Asn Ala
370                 375                 380
Gln Asp Leu Leu Pro Thr Gly Ser Tyr Ile Gly Leu Glu Leu Gly Lys
385                 390                 395                 400
Val Val Glu Leu Val Ile Pro Pro Leu Ala Val Gly Gly Pro His Pro
                405                 410                 415
Phe His Leu His Gly His Asn Phe Trp Val Val Arg Ser Ala Gly Ser
            420                 425                 430
Asp Glu Tyr Asn Phe Asp Asp Ala Ile Leu Arg Asp Val Val Ser Ile
        435                 440                 445
Gly Ala Gly Thr Asp Glu Val Thr Ile Arg Phe Val Thr Asp Asn Pro
    450                 455                 460
Gly Pro Trp Phe Leu His Cys His Ile Asp Trp His Leu Glu Ala Gly
465                 470                 475                 480
Leu Ala Ile Val Phe Ala Glu Gly Ile Asn Gln Thr Ala Ala Ala Asn
                485                 490                 495
Pro Thr Pro Gln Ala Trp Asp Glu Leu Cys Pro Lys Tyr Asn Gly Leu
            500                 505                 510
Ser Ala Ser Gln Lys Val Lys Pro Lys Lys Gly Thr Ala Ile
        515                 520                 525

<210> SEQ ID NO 3
<211> LENGTH: 2299
<212> TYPE: DNA
<213> ORGANISM: Cerrena unicolor

<400> SEQUENCE: 3
gatctggacg atggtatata agacgatggt atgagaccca tgaagtctga acacttttgc      60
tctctgacat tcatggttc atactctcga gatgggattg aactcggcta ttacatcgct      120
tgctatctta gctctgtcag tcggaagcta tgctgcaatt gggcccgtgg ccgacataca      180
cattgtcaac aaagaccttg ctccagatgg tgtacaacgt ccaaccgtgc tcgccggagg      240
cactttcct gggacgttga tcaccggtca gaaagtaagg aatattagtt tgcgtcaaag      300
agccaaccaa aattaaccgt cccgtcccat agggtgacaa cttccagctc aatgtcattg      360
atgatcttac cgacgatcgg atgttgacac caacttccat tgtgagccta ttattgtatg      420
atttatccgt atagtttctc agtctgatca ttggctctct atcgctagca ttggcacggt      480
ttcttccaga agggaaccgc ttgggccgac ggtcccgcct tcgtaactca gtgccctata      540
atagcagata actctttct gtatgacttc gacgtcccg accaagctgg tacttctgg      600
tatcatagtc atctatccac tcagtactgt gacggtttac gtggtgcctt cgttgtgtac      660
gatcctaacg atcctcacaa agacctatac gatgttgatg acggtgggtt ccaaatactt      720
gaccaagaaa cattatattg atagtatcca ctctgatttt cagagagcac cgtgattacc      780
```

-continued

```
cttgcggatt ggtaccatgt tctcgcccag accgttgtcg gcgctgcgtg agtaacacat      840
acacgcgctc cggcacactg atactaattt tttattgtag cactcctgat tctaccttga      900
tcaacgggtt aggccgttca cagaccggac ccgctgatgc tgagctggct gttatcagcg      960
ttgaacataa caaacggtat gtcatctcta cccattatct tctctcctgc tttaattcgc     1020
tgtttcacca tagataccga ttccgtttgg tttcgatttc gtgcgacccc aactttacct     1080
tctccgttga tggtcataat atgactgtca tcgaagtcga cggtgtcaac acacgacccc     1140
tgaccgttga ctctattcaa atcttcgccg acagaggta ttcctttgtc gtaagttaat     1200
cgatatattc tccctattac ccctgtgtaa ttgatgtcaa cagctcaatg ctaaccaacc     1260
cgacgacaat tactggatcc gtgctatgcc aaacatcggt agaaatacaa caacactgga     1320
cggaaagaat gccgctatcc ttcgatacaa gaatgcttct gtagaagagc ccaagaccgt     1380
tgggggcccc gctcaatccc cgttgaatga agcggacctg cgtccactcg tacctgctcc     1440
tgtggtatgt cttgtcgtgc tgttccatcg ctatttcata ttaacgtttt gtttttgtca     1500
agcctggaaa cgctgttcca ggtggcgcag acatcaatca caggcttaac ttaactttcg     1560
tacgtacacc tggttgaaac attatatttc cagtctaacc tcttgtagag taacggcctt     1620
ttcagcatca acaacgcctc cttcactaat ccttcggtcc ccgccttatt acaaattctg     1680
agcggtgctc agaacgctca agatttactt ccaacgggta gttacattgg ccttgaacta     1740
ggcaaggttg tggagctcgt tatacctcct ctggcagttg gaggaccgca cccttccat     1800
cttcatggcg taagcatacc acactcccgc agccagaatg acgcaaacta atcatgatat     1860
gcagcacaat ttctgggtcg tccgtagtgc aggtagcgat gagtataact ttgacgatgc     1920
tatcctcagg gacgtcgtga gcattggagc ggggactgat gaagtcacaa tccgtttcgt     1980
ggtatgtctc accctcgca ttttgagacg caagagctga tatattttaa catagaccga     2040
caatccgggc ccgtggttcc tccattgcca tattgattgg catttggagg caggccttgc     2100
catcgtcttc gctgagggca tcaatcagac cgctgcagcc aacccaacac cccgtacgtg     2160
acactgaggg tttctttata gtgctggatt actgaatcga gatttctcca cagaagcatg     2220
ggatgagctt tgccccaaat ataacggggtt gagtgcgagc cagaaggtca agcctaagaa     2280
aggaactgct atttaaacg                                                  2299
```

<210> SEQ ID NO 4
<211> LENGTH: 526
<212> TYPE: PRT
<213> ORGANISM: Cerrena unicolor

<400> SEQUENCE: 4

```
Met Gly Leu Asn Ser Ala Ile Thr Ser Leu Ala Ile Leu Ala Leu Ser
1               5                   10                  15

Val Gly Ser Tyr Ala Ala Ile Gly Pro Val Ala Asp Ile His Ile Val
                20                  25                  30

Asn Lys Asp Leu Ala Pro Asp Gly Val Gln Arg Pro Thr Val Leu Ala
            35                  40                  45

Gly Gly Thr Phe Pro Gly Thr Leu Ile Thr Gly Gln Lys Gly Asp Asn
        50                  55                  60

Phe Gln Leu Asn Val Ile Asp Asp Leu Thr Asp Asp Arg Met Leu Thr
65                  70                  75                  80

Pro Thr Ser Ile His Trp His Gly Phe Phe Gln Lys Gly Thr Ala Trp
                85                  90                  95

Ala Asp Gly Pro Ala Phe Val Thr Gln Cys Pro Ile Ile Ala Asp Asn
            100                 105                 110
```

-continued

```
Ser Phe Leu Tyr Asp Phe Asp Val Pro Asp Gln Ala Gly Thr Phe Trp
        115                 120                 125
Tyr His Ser His Leu Ser Thr Gln Tyr Cys Asp Gly Leu Arg Gly Ala
130                 135                 140
Phe Val Val Tyr Asp Pro Asn Asp Pro His Lys Asp Leu Tyr Asp Val
145                 150                 155                 160
Asp Asp Gly Gly Thr Val Ile Thr Leu Ala Asp Trp Tyr His Val Leu
                165                 170                 175
Ala Gln Thr Val Val Gly Ala Ala Thr Pro Asp Ser Thr Leu Ile Asn
            180                 185                 190
Gly Leu Gly Arg Ser Gln Thr Gly Pro Ala Asp Ala Glu Leu Ala Val
        195                 200                 205
Ile Ser Val Glu His Asn Lys Arg Tyr Arg Phe Arg Leu Val Ser Ile
    210                 215                 220
Ser Cys Asp Pro Asn Phe Thr Phe Ser Val Asp Gly His Asn Met Thr
225                 230                 235                 240
Val Ile Glu Val Asp Gly Val Asn Thr Arg Pro Leu Thr Val Asp Ser
                245                 250                 255
Ile Gln Ile Phe Ala Gly Gln Arg Tyr Ser Phe Val Leu Asn Ala Asn
            260                 265                 270
Gln Pro Asp Asp Asn Tyr Trp Ile Arg Ala Met Pro Asn Ile Gly Arg
        275                 280                 285
Asn Thr Thr Thr Leu Asp Gly Lys Asn Ala Ala Ile Leu Arg Tyr Lys
    290                 295                 300
Asn Ala Ser Val Glu Glu Pro Lys Thr Val Gly Gly Pro Ala Gln Ser
305                 310                 315                 320
Pro Leu Asn Glu Ala Asp Leu Arg Pro Leu Val Pro Ala Pro Val Pro
                325                 330                 335
Gly Asn Ala Val Pro Gly Gly Ala Asp Ile Asn His Arg Leu Asn Leu
            340                 345                 350
Thr Phe Ser Asn Gly Leu Phe Ser Ile Asn Asn Ala Ser Phe Thr Asn
        355                 360                 365
Pro Ser Val Pro Ala Leu Leu Gln Ile Leu Ser Gly Ala Gln Asn Ala
    370                 375                 380
Gln Asp Leu Leu Pro Thr Gly Ser Tyr Ile Gly Leu Glu Leu Gly Lys
385                 390                 395                 400
Val Val Glu Leu Val Ile Pro Pro Leu Ala Val Gly Gly Pro His Pro
                405                 410                 415
Phe His Leu His Gly His Asn Phe Trp Val Val Arg Ser Ala Gly Ser
            420                 425                 430
Asp Glu Tyr Asn Phe Asp Asp Ala Ile Leu Arg Asp Val Val Ser Ile
        435                 440                 445
Gly Ala Gly Thr Asp Glu Val Thr Ile Arg Phe Val Thr Asp Asn Pro
    450                 455                 460
Gly Pro Trp Phe Leu His Cys His Ile Asp Trp His Leu Glu Ala Gly
465                 470                 475                 480
Leu Ala Ile Val Phe Ala Glu Gly Ile Asn Gln Thr Ala Ala Ala Asn
                485                 490                 495
Pro Thr Pro Gln Ala Trp Asp Glu Leu Cys Pro Lys Tyr Asn Gly Leu
            500                 505                 510
Ser Ala Ser Gln Lys Val Lys Pro Lys Lys Gly Thr Ala Ile
        515                 520                 525
```

```
<210> SEQ ID NO 5
<211> LENGTH: 1507
<212> TYPE: DNA
<213> ORGANISM: Artificial
<220> FEATURE:
<223> OTHER INFORMATION: synthetic fusion gene

<400> SEQUENCE: 5
ggatcctgaa gctatcggtc cggttgcaga tttacacatc gtaaacaaag atcttgcacc      60
tgacggcgtt caacgtccaa ctgtacttgc tggtggaaca ttccctggta cacttattac     120
tggtcaaaaa ggtgacaact tccaattaaa cgtaattgac gatcttacag atgaccgtat     180
gcttacaccg acttcaattc actggcacgg tttctttcaa aaaggaacag catgggctga     240
tggtcctgca ttcgttacac aatgtccaat cattgctgat aactctttcc tttacgattt     300
tgacgttcct gatcaagctg gtacattctg gtatcactca cacttatcca cacaatactg     360
cgatggactt cgcggagctt tcgtagttta cgacccaaac gatcctcata aagacctta      420
cgatgtagat gatggtggaa cagttatcac attagctgat tggtaccatg tacttgctca     480
aacagttgta ggtgcagcta caccagattc aacacttatc aatggattag gacgttctca     540
aactggtcct gctgacgcag aacttgctgt aatctctgtt gaacataaca aacgttacag     600
attccgtctt gttagcattt cttgcgatcc aaacttcaca ttttcagttg acggacataa     660
catgacagtt atcgaagtag atggtgtaaa cacacgtcca cttactgtag actctatcca     720
aatcttcgca ggacaacgtt actcattcgt attaaacgca aatcaaccag aagataacta     780
ctggattcgt gcaatgccaa acatcggacg taacactaca actcttgacg gcaaaaacgc     840
agctattctt cgttacaaaa acgcttctgt tgaagaacct aaaacagttg gtggaccagc     900
acaatcacca cttaacgaag ctgacttacg tccactggtt ccagcacctg tacctggaaa     960
cgctgtacca ggaggtgctg atattaatca tagacttaac cttactttct ctaacggtct    1020
gttctcaatc aacaacgctt cattcacaaa tccttcagtt ccagcacttt tacaaattct    1080
tagcggtgca caaaatgctc aggatctttt accaactgga tcttacattg gtcttgaact    1140
gggtaaagta gttgaattag taattcctcc gcttgctgta ggtggaccac atcctttcca    1200
tcttcacggt cataacttct gggttgtacg ttctgctggt tcagatgaat acaacttcga    1260
tgacgcaatt cttcgtgatg ttgtatctat tggtgctgga acagatgaag taactattcg    1320
tttcgtaaca gataaccctg gtccttggtt cttacattgt catatcgatt ggcatcttga    1380
agctggactt gctattgttt tcgctgaagg aatcaatcaa acagctgcag ctaacccaac    1440
acctcaagca tgggacgaat tatgtccaaa atacaacgca ctttctccag gagatactta    1500
aaagctt                                                               1507
```